United States Patent
Andernach et al.

(10) Patent No.: US 12,274,169 B2
(45) Date of Patent: Apr. 8, 2025

(54) COMPOUNDS WITH A FUROPYRROLE OR A THIENOPYRROLE GROUP, OPTOELECTRONIC COMPONENTS WITH SAID TYPE OF COMPOUND, AND USE OF SAID TYPE OF COMPOUND IN OPTOELECTRONIC COMPONENTS

(71) Applicant: HELIATEK GMBH, Dresden (DE)

(72) Inventors: Rolf Andernach, Ulm (DE); Olga Gerdes, Ulm (DE); Gunter Mattersteig, Ulm (DE); Ivan Ramirez, Dresden (DE); Antoine Mirloup, Ulm (DE)

(73) Assignee: HELIATEK GMBH, Dresden (DE)

( * ) Notice: Subject to any disclaimer, the term of this patent is extended or adjusted under 35 U.S.C. 154(b) by 0 days.

(21) Appl. No.: 17/621,300

(22) PCT Filed: Sep. 24, 2020

(86) PCT No.: PCT/DE2020/100826
§ 371 (c)(1),
(2) Date: Dec. 21, 2021

(87) PCT Pub. No.: WO2021/058065
PCT Pub. Date: Apr. 1, 2021

(65) Prior Publication Data
US 2022/0384731 A1 Dec. 1, 2022

(30) Foreign Application Priority Data
Sep. 24, 2019 (DE) .................... 10 2019 125 715.8

(51) Int. Cl.
*H10K 85/60* (2023.01)
*C07D 495/04* (2006.01)
*H10K 30/30* (2023.01)

(52) U.S. Cl.
CPC ......... *H10K 85/657* (2023.02); *C07D 495/04* (2013.01); *H10K 85/653* (2023.02);
(Continued)

(58) Field of Classification Search
CPC .................................................. H01L 51/00–56
See application file for complete search history.

(56) References Cited

U.S. PATENT DOCUMENTS 9,127,020 B2 * 9/2015 Hildebrandt ........ H01L 51/0068
11,063,222 B2 * 7/2021 Hildebrandt ........ H01L 51/0067
(Continued)

FOREIGN PATENT DOCUMENTS

DE 102004014046 A1 9/2004
DE 102013101712 A1 8/2014
(Continued)

*Primary Examiner* — Tamir Ayad
(74) *Attorney, Agent, or Firm* — LEYDIG, VOIT & MAYER, LTD.

(57) ABSTRACT

The invention relates to a compound of the general formula I

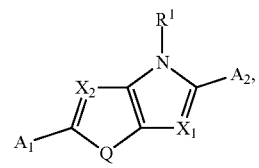

to an optoelectronic component containing said type of compound, and to the use of said type of compound in optoelectronic components.

12 Claims, 10 Drawing Sheets

(52) U.S. Cl.
CPC ......... *H10K 85/655* (2023.02); *H10K 85/656* (2023.02); *H10K 30/30* (2023.02)

(56) References Cited

U.S. PATENT DOCUMENTS

| | | |
|---|---|---|
| 2007/0090371 A1 | 4/2007 | Drechsel |
| 2013/0160829 A1 | 6/2013 | Uhrich |
| 2019/0006599 A1 | 1/2019 | Hildebrandt |
| 2019/0019957 A1 | 1/2019 | Hildebrandt |

FOREIGN PATENT DOCUMENTS

| | | |
|---|---|---|
| WO | WO 2011161108 A1 | 12/2011 |
| WO | WO 2014128277 A1 | 8/2014 |
| WO | WO 2017114937 A1 | 7/2017 |
| WO | WO 2017114938 A1 | 7/2017 |

\* cited by examiner

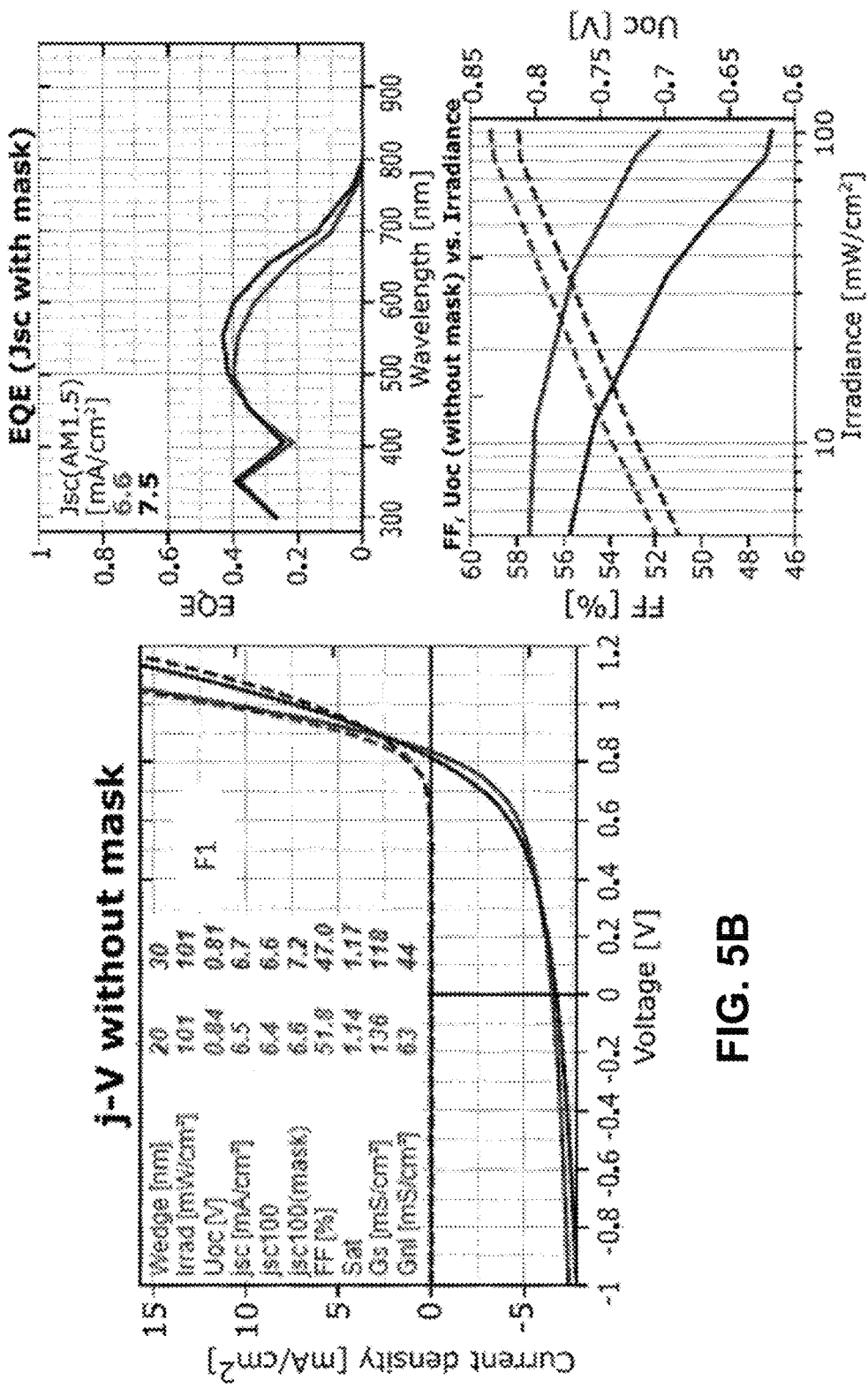

COMPOUNDS WITH A FUROPYRROLE OR A THIENOPYRROLE GROUP, OPTOELECTRONIC COMPONENTS WITH SAID TYPE OF COMPOUND, AND USE OF SAID TYPE OF COMPOUND IN OPTOELECTRONIC COMPONENTS

CROSS-REFERENCE TO PRIOR APPLICATIONS

This application is a U.S. National Phase application under 35 U.S.C. § 371 of International Application No. PCT/DE2020/100826, filed on Sep. 24, 2020, and claims benefit to German Patent Application No. DE 10 2019 125 715.8, filed on Sep. 24, 2019. The International Application was published in German on Apr. 1, 2021 as WO 2021/058065 under PCT Article 21(2).

FIELD

The present invention relates to compounds of the general formula I, to optoelectronic components comprising a compound of said type, and to the use of a compound of said type in optoelectronic components.

BACKGROUND

Circuitry made from electrically conductive polymers or small organic molecules is often used for optoelectronic components. Optoelectronic components can for example be displays, data memories or transistors, but also organic optoelectronic components, in particular organic photoactive components, for example solar cells and photodetectors that have a photoactive layer in which incident electromagnetic radiation results in the generation of charge carriers, particularly bound electron-hole pairs (excitons).

Organic optoelectronic components enable the conversion of electromagnetic radiation into electrical current by making use of the photoelectric effect. A conversion of electromagnetic radiation of this kind requires absorber materials that show good absorption properties. Further optoelectronic components are light-emitting electroluminescent components that emit light when electrical current flows through them. Optoelectronic components comprise at least two electrodes, one electrode being applied to a substrate and the other functioning as a counter electrode; between the electrodes there is at least one layer system, the layer system having at least one organic photoactive layer. Further layers, for example charge carrier transport layers, can additionally be arranged between the electrodes.

A structure of an organic solar cell known from the prior art consists of a pin or nip structure (Martin Pfeiffer, "Controlled doping of organic vacuum deposited dye layers: basics and applications", Ph.D. thesis TU-Dresden, 1999, and WO2011/161108A1). A pin solar cell consists of a substrate followed by mostly transparent electrode, p-layer(s), i-layer(s), n-layer(s), and a counter electrode, and a nip solar cell consists of a substrate followed by mostly transparent electrode, n-layer(s), i-layer(s), p-layer(s), and a counter electrode.

Numerous absorber materials for organic solar cells are known from the prior art.

WO2017114937A1 discloses an organic compound, the organic compound being characterized by high absorption in the short-wave spectral range of visible light. The use of this compound for an organic electronic component and a method for preparing the compound are also disclosed.

WO2017114938A1 discloses an organic semiconducting material and the use thereof in organic components in which the organic material can serve as a functional component in organic electronic components, resulting in improved absorption in organic solar cells, or exhibits increased charge carrier mobility.

Although the absorber materials disclosed in the prior art are suitable for photoactive layers in organic photovoltaic elements, i.e. organic solar cells, the absorption properties of the absorber materials are in need of improvement, especially in order to make organic photovoltaic elements (OPVs) competitive with conventional silicon-based solar cells. The efficiency of an organic photovoltaic element depends inter alia on the absorption behavior of the organic compounds, that is to say the absorber materials, in the at least one photoactive layer. It is advantageous here, particularly in tandem, triple or multiple cells, for there to be a high total absorption and an absorption in a broad region of the available spectrum of electromagnetic radiation by virtue of a plurality of absorber materials that absorb in different wavelength ranges, since this allows photons of different wavelengths to be utilized for the generation of electrical power. The individual cells of the tandem, triple or multiple cells should have an open-circuit voltage of the same magnitude, in particular within a range from 0.9 to 1.1 V.

Disadvantages of the prior art are in particular the absorption properties of absorber materials in the blue/green range of visible light, high absorption coefficients in particular being required for the construction of solar cells having open-circuit voltages Uoc in the range from 0.9 V to 1.1 V. At wavelengths in the 500 nm to 600 nm range, the absorption of known organic compounds suitable for organic photovoltaic elements is insufficient. This is disadvantageous particularly in the construction of tandem, triple, and multiple cells, since the individual sub-cells do not exhibit efficiency and open-circuit voltage of the same magnitude, that is to say one sub-cell supplies a lower open-circuit voltage than another sub-cell, which means that one sub-cell makes only a relatively small contribution to the efficiency of the component.

SUMMARY

A compound of the general formula I

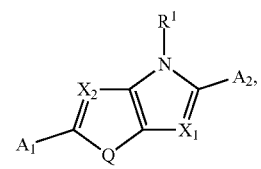

wherein:

Q is O or S;

R1 is selected from the group consisting of alkoxy, alkyl, fluorinated alkyl, partially fluorinated alkyl, and aryl;

X1 and X2 are independently of one another N or C—R4; where

R4 is selected from the group consisting of H, halogen, alkoxy, branched or linear, cyclic or open-chain alkyl, alkenyl, and aryl, wherein H may in each case be substituted;

A1 is a group having the formula Ia

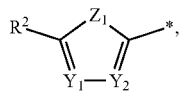

where * denotes the point of attachment to the compound of the general formula I;

Z1 is selected from the group consisting of O, S, Se, and N—R5, where R5 is selected from the group consisting of H, alkoxy, alkyl, fluorinated alkyl, partially fluorinated alkyl, and aryl;

Y1 is N or C—R6, where R6 is selected from the group consisting of H, halogen, alkoxy, branched or linear, cyclic or open-chain alkyl, alkenyl, and aryl, wherein H may in each case be substituted;

Y2 is N or C—R7, where R7 is selected from the group consisting of H, halogen, alkoxy, branched or linear, cyclic or open-chain alkyl, alkenyl, and aryl, wherein H may in each case be substituted; and where R6 and R7 may be homocyclically or heterocyclically linked to one another in the form of a ring structure;

R2 is selected from the group consisting of H, halogen, alkoxy, alkyl, fluorinated alkyl, partially fluorinated alkyl, branched or linear, cyclic or open-chain alkyl, amino, aryl, heteroaryl, alkenyl, and an electron-withdrawing alkyl group having at least one C=C double bond, wherein H may be substituted by CN or F;

A2 is a group having the formula Ib

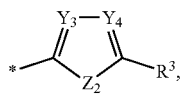

where * denotes the point of attachment to the compound of the general formula I;

Z2 is selected from the group consisting of O, S, Se, and N—R8, where R8 is selected from the group consisting of H, alkoxy, alkyl, fluorinated alkyl, partially fluorinated alkyl, and aryl;

Y3 is N or C—R9, where R9 is selected from the group consisting of H, halogen, alkoxy, branched or linear, cyclic or open-chain alkyl, alkenyl, and aryl, wherein H may in each case be substituted;

Y4 is N or C—R10, where R10 is selected from the group consisting of H, halogen, alkoxy, branched or linear, cyclic or open-chain alkyl, alkenyl, and aryl, wherein H may in each case be substituted; and where R9 and R10 may be homocyclically or heterocyclically linked to one another in the form of a ring structure; and R3 is selected from the group consisting of H, halogen, alkoxy, alkyl, fluorinated alkyl, partially fluorinated alkyl, branched or linear, cyclic or open-chain alkyl, amino, aryl, heteroaryl, alkenyl, and an electron-withdrawing alkyl group having at least one C=C double bond, wherein H may be substituted by CN or F.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following:

FIGS. 5A, 5B, 5C, and 5D show a graphical representation of the absorption spectrum of comparison compound F1, and of the current-voltage curve, of the spectral external quantum yield, and of the fill factor of a BHJ cell comprising the comparison compound F1, measured on an organic optoelectronic component in the form of an organic solar cell;

DETAILED DESCRIPTION

Figure 1:
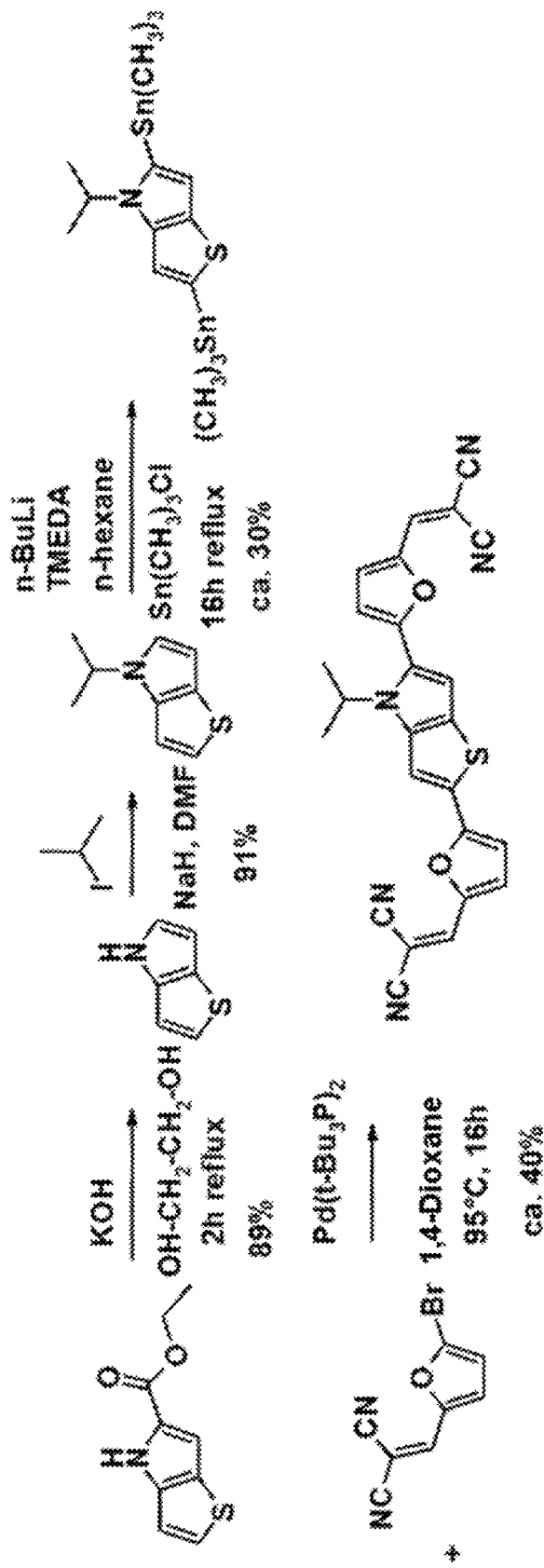
FIG. 1 shows an exemplary embodiment of a synthesis scheme for the synthesis of compounds of the invention.

The object of the invention is therefore to provide organic compounds for use in organic optoelectronic components, an optoelectronic component comprising at least one compound of said type, and for the use of compounds of said type in an optoelectronic component in which the disadvantages mentioned are absent and the organic compounds show improved absorption properties in particular.

The object is achieved by the subjects of the independent claims. Advantageous embodiments arise from the dependent claims.

The object is achieved in particular by providing a compound of the general formula I,

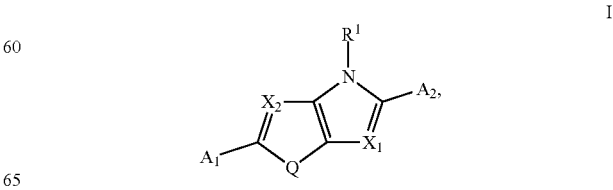

characterized in that

Q is O or S, preferably Q is S;

R1 is selected from the group consisting of alkoxy, alkyl, fluorinated alkyl, partially fluorinated alkyl, and aryl;

X1 and X2 are independently of one another N or C—R4; where

R4 is selected from the group consisting of H, halogen, alkoxy, branched or linear, cyclic or open-chain alkyl, alkenyl, and aryl, wherein H may in each case be substituted;

A1 is a group having the formula Ia

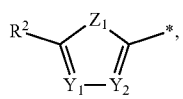

where * denotes the point of attachment to the compound of the general formula I;

Z1 is selected from the group consisting of O, S, Se, and N—R5, where R5 is selected from the group consisting of H, alkoxy, alkyl, fluorinated alkyl, partially fluorinated alkyl, and aryl;

Y1 is N or C—R6, where R6 is selected from the group consisting of H, halogen, alkoxy, branched or linear, cyclic or open-chain alkyl, alkenyl, and aryl, wherein H may in each case be substituted;

Y2 is N or C—R7, where R7 is selected from the group consisting of H, halogen, alkoxy, branched or linear, cyclic or open-chain alkyl, alkenyl, and aryl, wherein H may in each case be substituted; and where R6 and R7 may be homocyclically or heterocyclically linked to one another in the form of a ring structure;

R2 is selected from the group consisting of H, halogen, alkoxy, alkyl, fluorinated alkyl, partially fluorinated alkyl, branched or linear, cyclic or open-chain alkyl, amino, aryl, heteroaryl, alkenyl, and an electron-withdrawing alkyl group having at least one C=C double bond, wherein H may be substituted by CN or F;

A2 is a group having the formula Ib

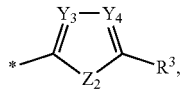

where * denotes the point of attachment to the compound of the general formula I;

Z2 is selected from the group consisting of O, S, Se, and N—R8, where R8 is selected from the group consisting of H, alkoxy, alkyl, fluorinated alkyl, partially fluorinated alkyl, and aryl;

Y3 is N or C—R9, where R9 is selected from the group consisting of H, halogen, alkoxy, branched or linear, cyclic or open-chain alkyl, alkenyl, and aryl, wherein H may in each case be substituted;

Y4 is N or C—R10, where R10 is selected from the group consisting of H, halogen, alkoxy, branched or linear, cyclic or open-chain alkyl, alkenyl, and aryl, wherein H may in each case be substituted; and where R9 and R10 may be homocyclically or heterocyclically linked to one another in the form of a ring structure; and R3 is selected from the group consisting of H, halogen, alkoxy, alkyl, fluorinated alkyl, partially fluorinated alkyl, branched or linear, cyclic or open-chain alkyl, amino, aryl, heteroaryl, alkenyl, and an electron-withdrawing alkyl group having at least one C=C double bond, wherein H may be substituted by CN or F.

In a preferred embodiment of the invention, Q is S.

The present invention relates in particular to A-D-A dyes of the compound of the general formula I having a central furopyrrole moiety or a central thienopyrrole moiety.

In a preferred embodiment of the invention, X1 and X2 are H.

In a preferred embodiment of the invention, the group having the formula Ia and/or the group having the formula Ib is a furan or a furan derivative.

In a preferred embodiment of the invention, the group having the formula Ia and/or the group having the formula Ib is a thiophene or a thiophene derivative.

In a preferred embodiment of the invention, the group having the formula Ia and/or the group having the formula Ib is a pyrrole or a pyrrole derivative.

In a preferred embodiment of the invention, the group having the formula Ia and/or the group having the formula Ib is a thiazole or a thiazole derivative.

In a preferred embodiment of the invention, the group having the formula Ia and/or the group having the formula Ib is a thiadiazole or a thiadiazole derivative.

In a preferred embodiment of the invention, the group having the formula Ia and/or the group having the formula Ib is an oxazole or an oxazole derivative.

In a preferred embodiment of the invention, the group having the formula Ia and/or the group having the formula Ib is an imidazole or an imidazole derivative.

In a preferred embodiment of the invention, the group having the formula Ia and/or the group having the formula Ib is a triazole or a triazole derivative.

In a preferred embodiment of the invention, the group having the formula Ia and/or the group having the formula Ib is an oxadiazole or an oxadiazole derivative.

In a preferred embodiment of the invention, at least two of the groups A1, A2, A3 or A4 are a furan, a thiophene, a pyrrole, a thiazole, a thiadiazole, an oxazole, an imidazole, a triazole, or an oxadiazole, or a derivative thereof.

In the context of the present invention, a derivative is understood as meaning in particular a compound derived from a basic structure or a radical, in which individual atoms or groups are modified or substituted based on the original compound.

In a preferred embodiment of the invention, a furan and/or a thiophene group, in particular a furan group, is arranged on the furopyrrole moiety or on the thienopyrrole moiety, in particular on the thienopyrrole moiety, and a sterically demanding group on the N of the pyrrole of the furopyrrole moiety or the thienopyrrole moiety, in particular isopropyl, isobutyl, sec-butyl, tert-butyl, isopentyl or phenyl. This improves the properties of the absorber materials in a particular way.

In a preferred embodiment of the invention, the central furopyrrole moiety or the central thienopyrrole moiety, in particular the pyrrole ring of the thienopyrrole moiety, has no further condensed aromatic system.

In a preferred embodiment of the invention, R5 and R6 are H.

In an alternatively preferred embodiment of the invention, the compound of the general formula I includes a homocyclic five-membered ring or six-membered ring respectively formed together by R5 and R6 and/or by R9 and R10, or a heterocyclic five-membered ring or six-membered ring containing at least one heteroatom selected from the group consisting of S, O, and N, wherein the five-membered ring or six-membered ring may be substituted in further positions.

An absorber material, that is to say an absorber, is understood as meaning in particular a compound that absorbs light in the >400 nm wavelength range. An absorber layer is accordingly understood as meaning in particular a layer in an optoelectronic component that includes at least one absorber material.

Figure 7:
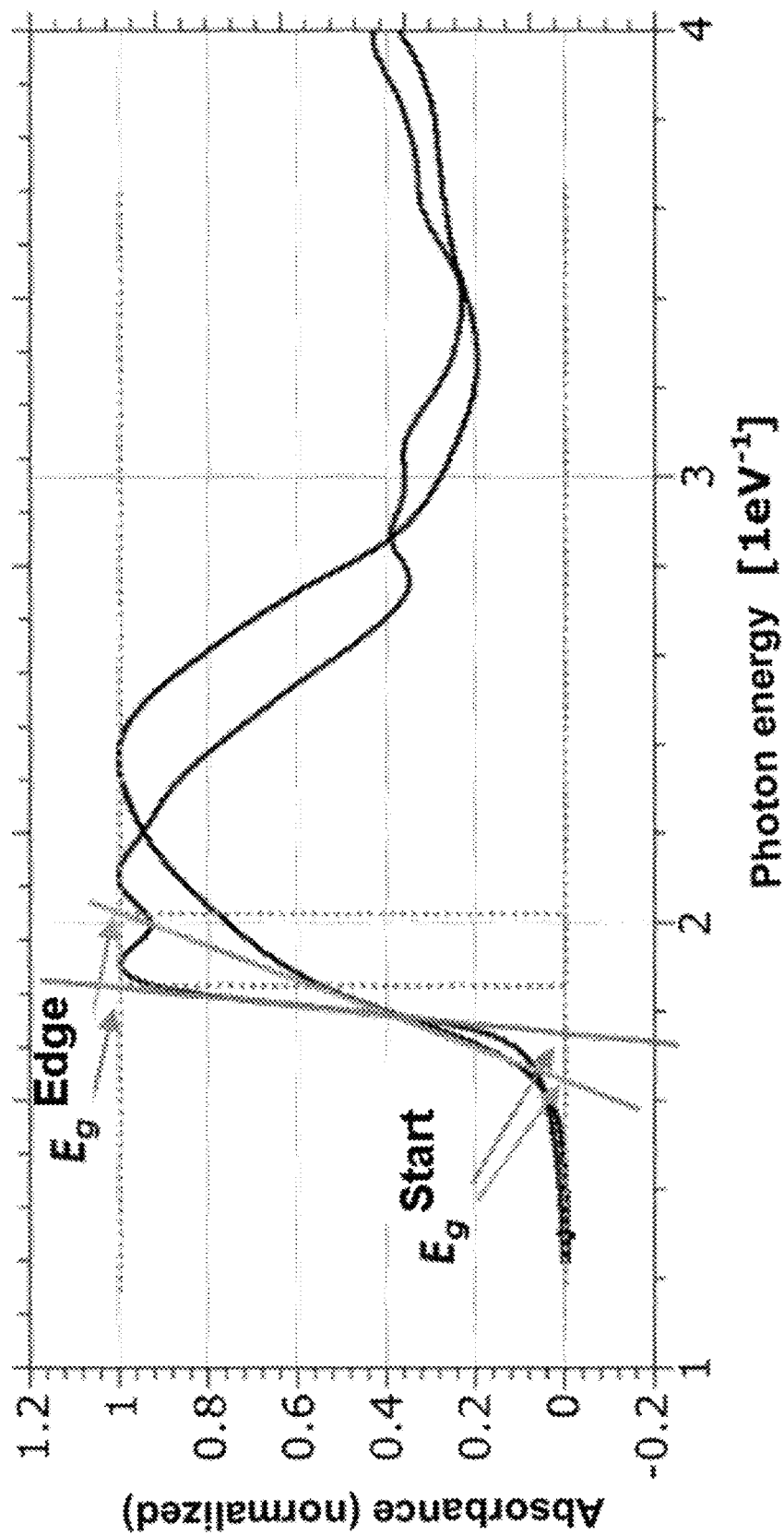
FIG. 7 shows an illustration of the determination of slope at an inflection point of the absorption spectrum. The slope of the curve in the absorption spectrum is determined via the gradient of the tangent at the inflection point that occurs between the start of the absorption and the first edge of the absorption (see, e.g., Wang et al., "Optical Gaps of Organic Solar Cells as a Reference for Comparing Voltage Losses", Adv. Energy Mater., 2018, 1801352).

A steep curve in the absorption spectrum, in particular a steep curve in the bathochromic region of the absorption spectrum, is understood as referring in particular to a slope at an inflection point of the absorption spectrum. The slope of the curve in the absorption spectrum is determined via the gradient of the tangent at the inflection point that occurs between the start of the absorption and the first edge of the absorption (Wang et al., "Optical Gaps of Organic Solar Cells as a Reference for Comparing Voltage Losses", Adv. Energy Mater., 2018, 1801352), cf. FIG. 7.

In a preferred embodiment of the invention, compounds of the invention exhibit a slope in the absorption spectrum of at least 5.6, preferably of at least 5.8, preferably of at least 6, preferably of at least 6.5, preferably of at least 7, preferably of at least 7.5, or preferably of at least 8.

Substitution is understood as meaning in particular the replacement of H by a substituent. A substituent is understood as meaning in particular all atoms and atomic groups except H, preferably a halogen, an alkyl group, it being possible for the alkyl group to be linear or branched, an amino group, a CN group, an alkenyl group, an alkynyl group, an alkoxy group, a thioalkoxy group, an aryl group, or a heteroaryl group. A halogen is understood in particular as meaning F, Cl or Br, preferably F.

A heteroatom is understood as meaning in particular an atom selected from the group consisting of O, S, Se, Si, B, N or P, preferably selected from the group consisting of O, S, Se or N, particularly preferably O or S.

In a preferred embodiment of the invention, none of the carbon atoms in an alkyl group has been replaced by a heteroatom.

The compounds of the invention relate in particular to so-called small molecules. Small molecules are understood as meaning in particular non-polymeric organic molecules having monodisperse molar masses between 100 and 2000 g/mol that exist in the solid phase at standard pressure (air pressure of the ambient atmosphere) and at room temperature. In particular, the small molecules are photoactive, photoactive being understood as meaning that the molecules undergo a change of charge state and/or of polarization state when light is supplied. The photoactive molecules show in particular an absorption of electromagnetic radiation within a defined wavelength range, wherein absorbed electromagnetic radiation, that is to say photons, are converted into excitons.

The compounds of the invention show in particular a high absorption coefficient, at least within a defined wavelength range. The compounds of the invention are used in particular in a donor-acceptor system having a heterojunction.

In a preferred embodiment of the invention, Y1, Y2, Y3, and Y4 are each independently of one another selected from the group consisting of N, CH, CF, C—CH$_3$, C—CF$_3$, C—C$_2$H$_5$, C—C$_3$H$_8$, C—OCH$_3$, C—OC$_2$H$_5$, C—SCH$_3$, C—SC$_2$H$_5$.

In a preferred embodiment of the invention, the cyclic or linear alkyl groups of the compounds of the invention are linear or branched, the alkyl groups preferably being linear C1-C5 alkyl groups.

In a preferred embodiment of the invention, at least one of positions Y1, Y2, Y3, and Y4 is an N, preferably at least one of positions Y1 and Y2 is an N, and at least one of positions Y3 and Y4 is an N. In a particularly preferred embodiment of the invention, positions Y1, Y2, Y3, and Y4 are in each case an N.

In a preferred embodiment of the invention, the positions Y1, Y2, Y3, and Y4 are in each case CH.

In a preferred embodiment of the invention, the compound of the general formula I has an O at position Z1 in formula Ia and an O at position Z2 in formula Ib. The absorption properties in particular are consequently more favorable than in comparable compounds having a different atom at these positions.

The compounds of the invention have advantages compared to the prior art. Advantageously, the compounds of the invention have surprisingly good absorption behavior in a comparatively broad spectral range of visible light, in particular a surprisingly high absorption was observed in the spectral range from approx. 500 nm to 600 nm. Advantageously, absorber materials having improved absorption in a wavelength range of the blue/green region of visible light are provided. Compounds of the invention advantageously show a particularly steep absorption curve in the bathochromic region. The compounds of the invention advantageously have sufficient thermal, chemical, and electrochemical stability to meet the demands typically placed on them in the manufacture and operation of photoactive organic electronic components, in particular, these compounds can be readily vaporized under reduced pressure. The compounds of the invention advantageously enable the construction of solar cells having an open-circuit voltage Uoc within a range from 0.9 to 1.1 V, in particular within a range from 0.95 V to 1.05 V.

According to a preferred embodiment of the invention, R1 is selected from the group consisting of ethyl, propyl, butyl, branched alkyl, and aryl, preferably from isopropyl, isobutyl, sec-butyl, isopentyl, tert-butyl and phenyl; and where Z1 and Z2 are each independently of one another O or S.

In a particularly preferred embodiment, Z2 is O. This realizes the advantageous effects of the present invention in a particular way.

According to a preferred embodiment of the invention, the compound is a compound of the general formula II,

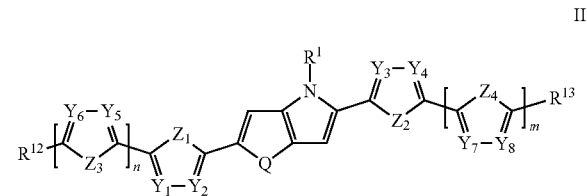

II where n is 0, 1 or 2 and m is 0, 1 or 2;

Q is O or S, preferably Q is S;

Z3 and Z4 are each independently of one another selected from the group consisting of O, S, Se, and N—R11, where R11 is selected from the group consisting of H, alkoxy, alkyl, fluorinated alkyl, partially fluorinated alkyl, and aryl;

R12 is selected from the group consisting of H, alkoxy, alkyl, fluorinated alkyl, partially fluorinated alkyl, alkenyl, and an electron-withdrawing alkyl group having at least one C═C double bond, wherein H may be substituted by CN or F;

R13 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F;

Y5 is N or C—R14, where R14 is selected from the group consisting of H, halogen, alkoxy, alkyl, and alkenyl, wherein H may in each case be substituted and where Y5 is preferably N, CH or CF;

Y6 is N or C—R15, where R15 is selected from the group consisting of H, halogen, alkoxy, alkyl, and alkenyl, wherein H may in each case be substituted and where Y6 is preferably N, CH or CF;

Y7 is N or C—R16, where R16 is selected from the group consisting of H, halogen, alkoxy, alkyl, and alkenyl, wherein H may in each case be substituted and where Y7 is preferably N, CH or CF;

Y8 is N or C—R17, where R17 is selected from the group consisting of H, halogen, alkoxy, alkyl, and alkenyl, wherein H may in each case be substituted and where Y8 is preferably N, CH or CF; and where respectively R14 and R15, and/or R16 and R17, may together form a homocyclic five-membered ring or six-membered ring, or a heterocyclic five-membered ring or six-membered ring containing at least one heteroatom selected from the group consisting of S, O, and N.

In a preferred embodiment of the invention, Z3 and Z4 are independently of one another O or S.

In a preferred embodiment of the invention, the compound of the general formula II has an O at position Z1 and an O at position Z2, and an O at position Z3 and/or an O at position Z4.

According to a preferred embodiment of the invention, A1 is a group having the formula IIa

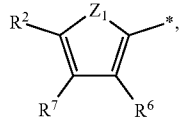

where R6 is selected from the group consisting of H, halogen, alkoxy, branched or linear, cyclic or open-chain alkyl, alkenyl, and aryl, wherein H may in each case be substituted;

R7 is selected from the group consisting of H, halogen, alkoxy, branched or linear, cyclic or open-chain alkyl, alkenyl, and aryl, wherein H may in each case be substituted; and where R6 and R7 may together form a homocyclic five-membered ring or six-membered ring, or a heterocyclic five-membered ring or six-membered ring containing at least one heteroatom selected from the group consisting of S, O and N;

and A2 is a group having the formula IIb

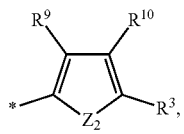

where R9 is selected from the group consisting of H, halogen, alkoxy, branched or linear, cyclic or open-chain alkyl, alkenyl, and aryl, wherein H may in each case be substituted;

R10 is selected from the group consisting of H, halogen, alkoxy, branched or linear, cyclic or open-chain alkyl, alkenyl, and aryl, wherein H may in each case be substituted; and where R9 and R10 may together form a homocyclic five-membered ring or six-membered ring, or a heterocyclic five-membered ring or six-membered ring containing at least one heteroatom selected from the group consisting of S, O and N.

In a particularly preferred embodiment of the invention, the compound is a compound of the general formula XIX

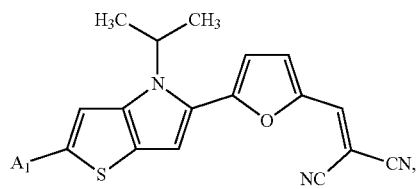

characterized in that
A1 is a group having the formula Ia

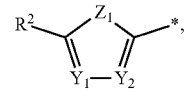

where * denotes the point of attachment to the compound of the general formula I;

Z1 is selected from the group consisting of O, S, Se, and N—R5, where R5 is selected from the group consisting of H, alkoxy, alkyl, fluorinated alkyl, partially fluorinated alkyl, and aryl;

Y1 is N or C—R6, where R6 is selected from the group consisting of H, halogen, alkoxy, branched or linear, cyclic or open-chain alkyl, alkenyl, and aryl, wherein H may in each case be substituted;

Y2 is N or C—R7, where R7 is selected from the group consisting of H, halogen, alkoxy, branched or linear, cyclic or open-chain alkyl, alkenyl, and aryl, wherein H may in each case be substituted; and where R6 and R7 may be homocyclically or heterocyclically linked to one another in the form of a ring structure;

R2 is selected from the group consisting of H, halogen, alkoxy, alkyl, fluorinated alkyl, partially fluorinated alkyl, branched or linear, cyclic or open-chain alkyl, amino, aryl, heteroaryl, alkenyl, and an electron-withdrawing alkyl group having at least one C=C double bond, wherein H may be substituted by CN or F.

In a preferred embodiment of the invention, positions Y1 and Y2 of the compound of the general formula XIX are in each case CH.

In a preferred embodiment of the invention, the compound of the general formula XIX has an O at position Z1 in formula Ia.

In a preferred embodiment of the invention, at least one of positions Y1 or Y2 of the compound of the general formula XIX is an N, preferably the positions Y1 and Y2 are an N.

According to a preferred embodiment of the invention, the compound is a compound of the general formula III, IV, and/or V,

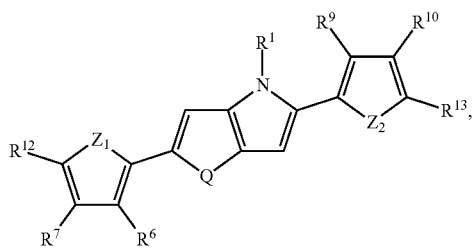

III

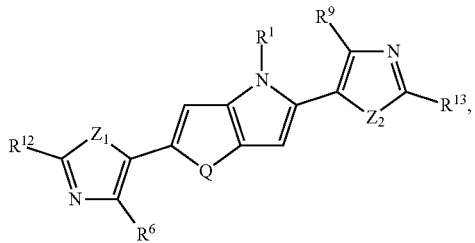

IV

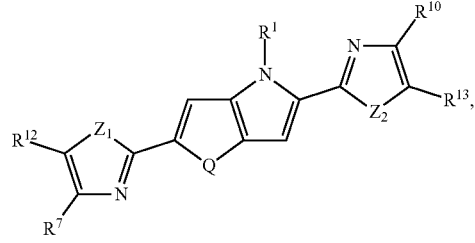

V

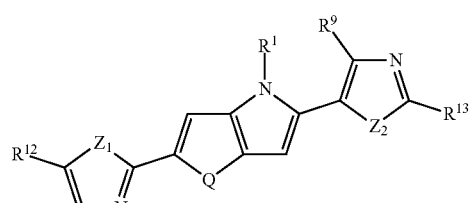

XX

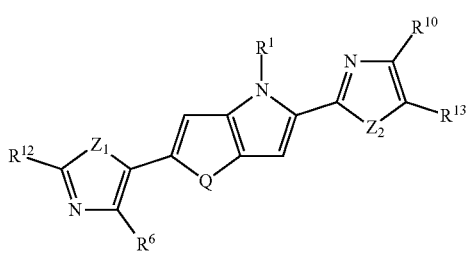

XXI

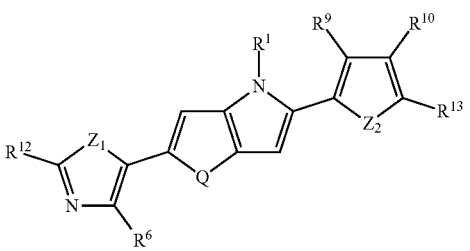

XXII

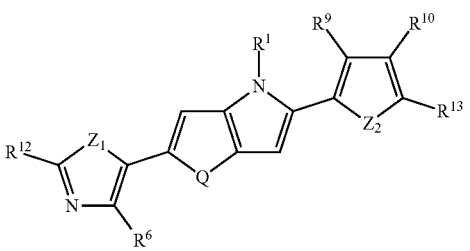

XXIII

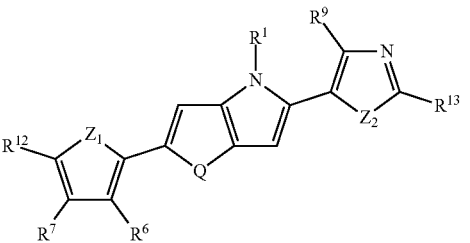

XXIV

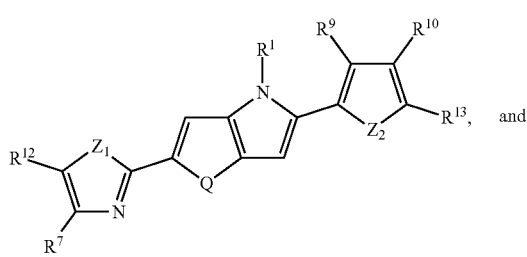

and

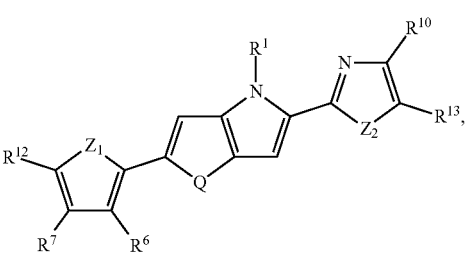

XXV where Q is O or S, preferably Q is S;

Z1 and Z2 are each independently of one another O or S, preferably Z2 is O;

R6 is selected from the group consisting of H, halogen, alkoxy, alkyl, and alkenyl, wherein H may in each case be substituted;

R7 is selected from the group consisting of H, halogen, alkoxy, alkyl, and alkenyl, wherein H may in each case be substituted; and where R6 and R7 may together form a homocyclic five-membered ring or six-membered ring, or a heterocyclic five-membered ring or six-membered ring containing at least one heteroatom selected from the group consisting of S, O and N;

R9 is selected from the group consisting of H, halogen, alkoxy, alkyl, and alkenyl, wherein H may in each case be substituted;

R10 is selected from the group consisting of H, halogen, alkoxy, alkyl, and alkenyl, wherein H may in each case be substituted; and where R9 and R10 may together form a homocyclic five-membered ring or six-membered ring, or a heterocyclic five-membered ring or six-membered ring containing at least one heteroatom selected from the group consisting of S, O and N;

R12 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F; and R13 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F.

In a preferred embodiment of the invention, the compound is a compound selected from the general formulas where Q is O or S, preferably Q is S;

Z1 and Z2 are each independently of one another O or S, preferably Z2 is O;

R6 is selected from the group consisting of H, halogen, alkoxy, alkyl, and alkenyl, wherein H may in each case be substituted;

R7 is selected from the group consisting of H, halogen, alkoxy, alkyl, and alkenyl, wherein H may in each case be substituted; and where R6 and R7 may together form a homocyclic five-membered ring or six-membered ring, or a heterocyclic five-membered ring or six-membered ring containing at least one heteroatom selected from the group consisting of S, O and N;

R9 is selected from the group consisting of H, halogen, alkoxy, alkyl, and alkenyl, wherein H may in each case be substituted;

R10 is selected from the group consisting of H, halogen, alkoxy, alkyl, and alkenyl, wherein H may in each case be substituted; and where R9 and R10 may together form a homocyclic five-membered ring or six-membered ring, or a heterocyclic five-membered ring or six-membered ring containing at least one heteroatom selected from the group consisting of S, O and N;

R12 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F; and R13 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F.

In a preferred embodiment of the invention, the compound is a compound of the general formulas VII and VIII,

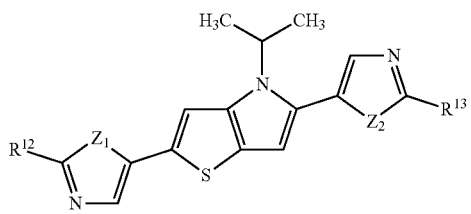

VII

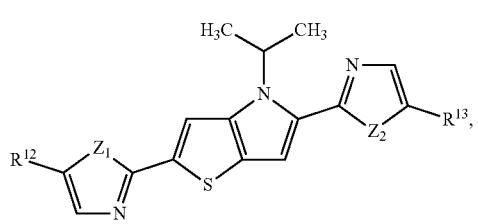

VIII where Z1 and Z2 are each independently of one another O or S,

R12 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F; and R13 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F.

According to a preferred embodiment of the invention, R2 and R3, or R12 and R13, are each independently of one another

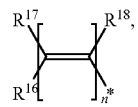

where n is 1, 2 or 3, where * denotes the point of attachment of the group R2, R3, R12 and/or R13;

R16, R17, and R18 are each independently of one another selected from the group consisting of H, halogen, CN, COO-alkyl, alkyl, and alkenyl, with the proviso that R16 and R17 are not both H, R16 and R17 preferably being CN. This realizes the advantageous effects of the present invention in a particular way.

In a preferred embodiment of the invention, R2 and/or R3, or R12 and/or R13, are/is each independently of one another

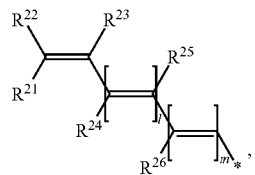

where m is 0, 1 or 2 and l is 0, 1 or 2; where * denotes the point of attachment of the group R2, R3, R12 and/or R13;

R21, R22, R23, R24, R25, and R26 are each independently of one another selected from the group consisting of H, halogen, CN, COO-alkyl, and alkenyl, with the proviso that R21 and R22 are not both H, R21 and R22 preferably being CN. A particularly good acceptor effect in groups R2 and/or R3, or R12 and/or R13, preferably can be achieved through a large number of CN groups.

According to a preferred embodiment of the invention,

R2 and R3, or R12 and R13, are each independently of one another selected from the group consisting of:

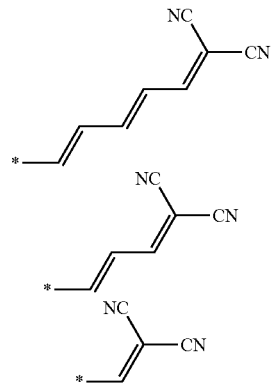

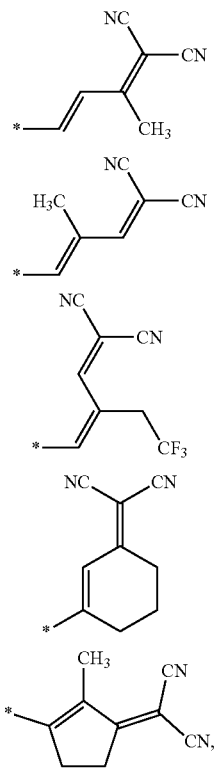

where * denotes the point of attachment of the group R2, R3, R12 and/or R13, in which CN may be replaced by F and where R2 and R3, or R12 and R13, are preferably identical.

According to a preferred embodiment of the invention, R6 and R7 are H, R9 and R10 are H, and Z2 is O; where Z1 and Z2 are preferably O. This realizes the advantageous effects of the present invention in a particular way.

In a preferred embodiment of the invention, R4 is H, R6 and R7 are H, and/or R9 and R10 are H, and Z1 and Z2 are O.

According to a preferred embodiment of the invention, the compound is selected from the group consisting of:

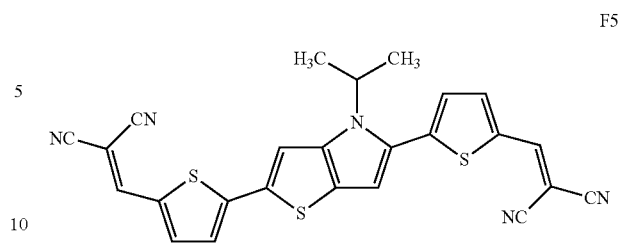

F3

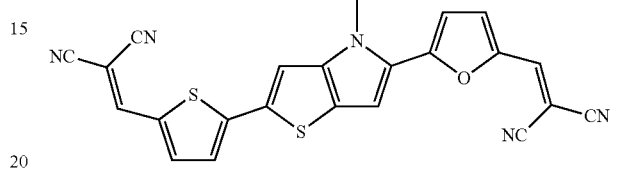

F4

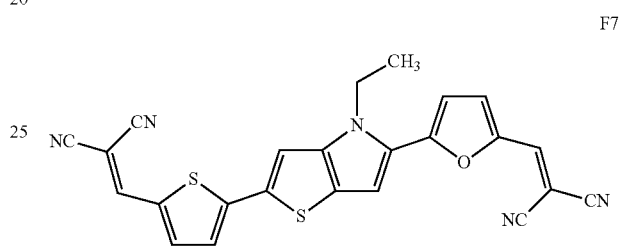

F5

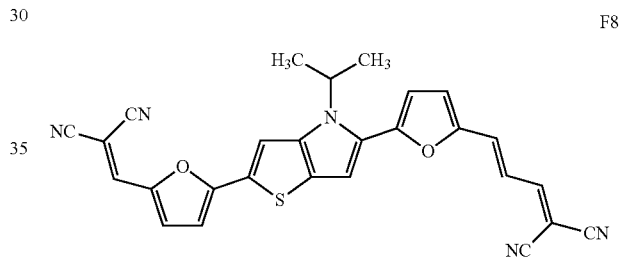

F6

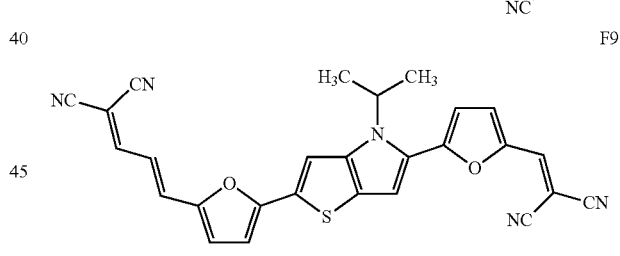

F7

F8

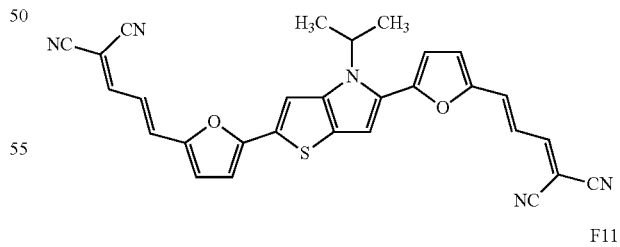

F9

F10

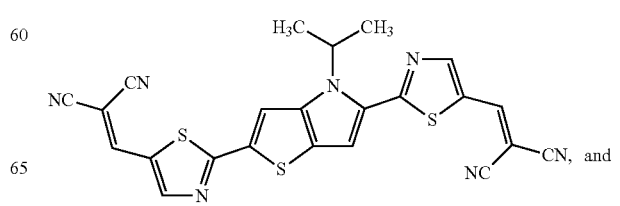

F11

, and

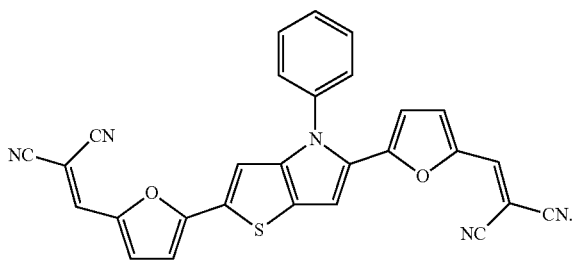

F12

In a preferred embodiment of the invention, R2 and/or R3, or R12 and/or R13, have at least two C═C double bonds.

According to a preferred embodiment of the invention, group A1 is the same as group A2.

In a particularly preferred embodiment of the invention, the compound is compound F3

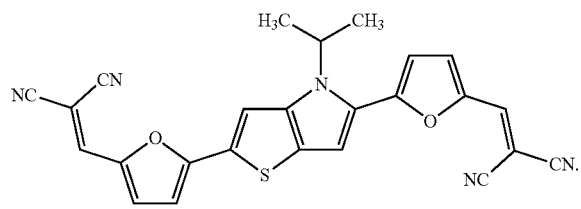

F3

In this compound, the advantageous absorption properties are realized to a particularly high degree.

In a particularly preferred embodiment of the invention, the compound is compound F6

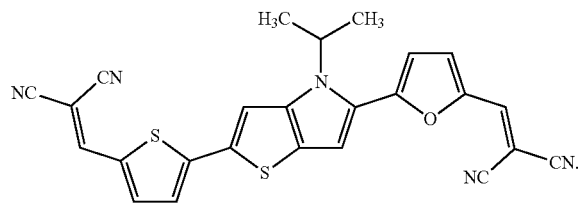

F6

In this compound, the advantageous absorption properties are realized to a particularly high degree.

In a particularly preferred embodiment of the invention, the compound is compound F12

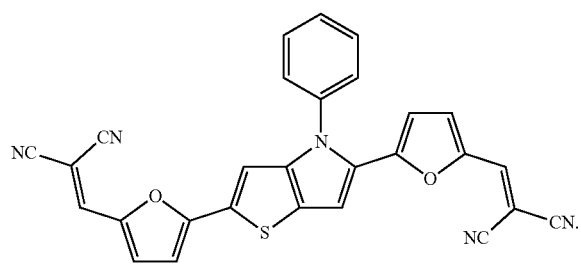

F12

In this compound, the advantageous absorption properties are realized to a particularly high degree.

Organic single or tandem cells are known from the prior art. DE102004014046A1 discloses a photoactive component, in particular a solar cell, consisting of organic layers of one or more pi, ni, and/or pin diodes stacked on top of one another. WO2011161108A1 discloses a photoactive component having an electrode and a counter electrode, wherein at least one organic layer system is arranged between the electrodes, having at least two photoactive layer systems and, between the photoactive layer systems, at least two different transport layer systems of the same charge-carrier type. One of the transport layer systems is energetically matched to one of the two photoactive layer systems, and the other transport layer system is transparent.

The object of the present invention is also achieved by providing an optoelectronic component comprising at least one compound of the invention, especially one according to one of the exemplary embodiments described above. For the optoelectronic component, this gives rise in particular to the advantages already elucidated in connection with the compound of the invention. The optoelectronic component comprises a first electrode, a second electrode, and a layer system, the layer system being arranged between the first electrode and the second electrode, characterized in that at least one layer of the layer system comprises at least one compound of the invention.

An organic optoelectronic component is understood as meaning in particular a component that comprises organic conductive or semiconductive materials, in particular a transistor, a light-emitting organic component, an organic photovoltaic element (OPV), in particular an organic solar cell, or a photodetector. Organic photovoltaic cells comprising at least one compound of the invention allow particularly efficient utilization of the visible light spectrum.

An organic photovoltaic element (OPV) is understood as meaning in particular a photovoltaic element, in particular a solar cell, having at least one organic photoactive layer, the organic photoactive layer comprising at least one compound of the invention. An organic photovoltaic element allows electromagnetic radiation, particularly in the visible light wavelength range, to be converted into electrical current by making use of the photoelectric effect.

According to a preferred embodiment of the invention, the optoelectronic component is an organic optoelectronic component, preferably an organic solar cell, an OFET, an OLED or an organic photodetector.

According to a preferred embodiment of the invention, the layer system has at least one photoactive layer, preferably an absorber layer, wherein the at least one photoactive layer comprises the at least one compound of the invention.

The organic electronic component comprises in particular an electrode and a counter electrode, there being an organic photoactive layer arranged between the electrodes. The organic photoactive layer is in particular a photoactive layer in which excitons (electron-hole pairs) are formed by radiation from visible light, UV radiation, and/or IR radiation. The organic materials are printed, glued, coated, vapor-deposited or otherwise applied onto the foils in the form of thin films or small volumes. All processes that are also used for electronics on glass, ceramic or semiconducting substrates can likewise be used for producing the thin layers. The organic photoactive layer has a function that is important for the optoelectronic component, in particular a charge-carrier transport function such as the transport of holes (p-conducting) or the transport of electrons (n-conducting).

According to a preferred embodiment of the invention, the layer system has at least two photoactive layers, preferably at least three photoactive layers, or preferably at least four photoactive layers, the photoactive layers preferably being absorber layers. In a preferred embodiment of the invention, the at least one photoactive layer is arranged between the first electrode and the second electrode.

In a preferred embodiment of the invention, the organic solar cell has a photoactive layer that comprises at least one organic donor material in contact with at least one organic acceptor material, the donor material and the acceptor material forming a donor-acceptor heterojunction, in particular a so-called bulk heterojunction (BHJ), and wherein the photoactive layer comprises at least one compound of the invention.

In a preferred embodiment of the invention, the optoelectronic component comprises at least one further layer, preferably at least one charge-transport layer, in particular an electron-transport layer and/or a hole-transport layer.

In a preferred embodiment of the invention, the at least one charge-transport layer, in particular at least one electron-transport layer and/or at least one hole-transport layer, comprises the at least one compound of the invention.

In a preferred embodiment of the invention, the optoelectronic component comprises a substrate, the first electrode or the second electrode being arranged on the substrate, in particular it is possible for one of the electrodes of the optoelectronic component to have been directly applied to the substrate, the layer system being arranged between the first electrode and the second electrode.

In a preferred embodiment of the invention, the organic solar cell is a single, tandem, triple, quadruple or other multiple cell.

A tandem cell is understood in particular as meaning that two functional cells are spatially stacked on top of one another and connected in series, preferably between a first electrode and a second electrode, wherein one or more intermediate layers may be arranged between the cells. A triple, quadruple or other multiple cell is accordingly understood as meaning that more than two functional cells are spatially stacked on top of one another and connected in series, wherein an intermediate layer may be arranged between the cells.

According to a preferred embodiment of the invention, the photoactive layer is formed as a mixed layer of the at least one compound of the invention and at least one further compound, or as a mixed layer of the at least one compound of the invention and at least two further compounds, the compounds being absorber materials.

In a preferred embodiment of the invention, the optoelectronic component is formed as a nip, ni, ip, pnip, pni, pip, nipn, nin, ipn, pnipn, or pipn cell, or formed as a combination of nip, ni, ip, pnip, pni, pip, nipn, nin, ipn, pnipn, or pipn cells.

In a particularly preferred embodiment of the invention, the optoelectronic component is formed as a mip cell, or formed as a combination of a mip cell with a nip, ni, ip, pnip, pni, pip, nipn, nin, ipn, pnipn, or pipn cell.

An i-layer is understood as meaning in particular an intrinsic undoped layer. One or more i-layers may here consist of one material (planar heterojunctions, PHJ) or else of a mixture of two or more materials (bulk heterojunctions, BHJ) that comprise an interpenetrating network.

In a preferred embodiment, the compound of the invention and/or a layer comprising the at least one compound of the invention can be deposited by means of vacuum processing, gas-phase deposition or solvent processing, particularly preferably by means of vacuum processing.

The object of the present invention is also achieved by providing for the use of a compound of the invention in an optoelectronic component, preferably in an organic optoelectronic component, in particular according to one of the exemplary embodiments described above. The use of the compound of the invention in an optoelectronic component gives rise in particular to the advantages that have already been elucidated in connection with the compound of the invention and with the optoelectronic component comprising the at least one compound of the invention.

In a preferred embodiment of the invention, the optoelectronic component is an organic optoelectronic component, preferably an organic solar cell.

Some exemplary embodiments of compounds of the invention and non-inventive compounds (F1 and F2) with their optical properties are shown below. Table 1 shows an overview of the melting points and absorption maxima (in nm and eV in the solvent (SO)) of these compounds. The spectral data relate to vacuum vapor-deposition layers on quartz glass having a thickness of 30 nm. The associated absorption spectra of compounds F3 and F12 listed in Table 1 are shown in FIGS. 3 and 4 and a comparison with the comparison compound F1 is shown in FIG. 5.

TABLE 1

| No. | Structure | m.p./° C.[a] approx. | λmax (SO)/nm[b] | λmax (SO)/eV[b] |
|---|---|---|---|---|
| F1 | 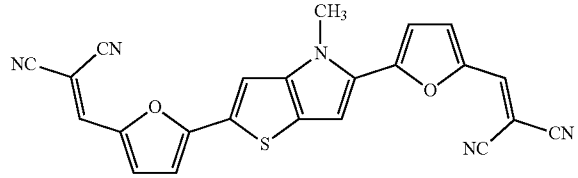 | 370° C. | 562[c] | 2.21[c] |
| F2 | 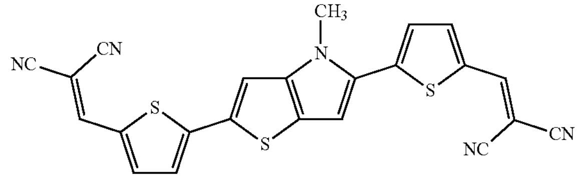 [SMILES: Cn1c(-c2ccc(C=C(C#N)C#N)o2)cc2sc(-c3ccc(C=C(C#N)C#N)o3)cc21] | 349 | 555[b] | 2.23[b] |

TABLE 1-continued

| No. | Structure | m.p./° C.[a] approx. | λmax (SO)/nm[b] | λmax (SO)/eV[b] |
|---|---|---|---|---|
| F3 | 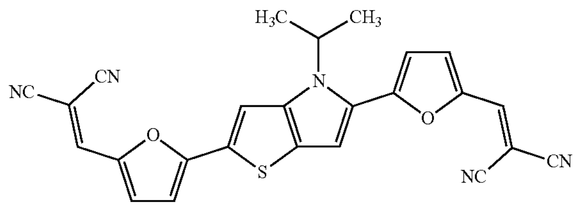 [SMILES: CC(C)n1c(-c2ccc(C=C(C#N)C#N)o2)cc2sc(-c3ccc(C=C(C#N)C#N)o3)cc21] | 356 | 569[b] | 2.18[b] |
| F4 | 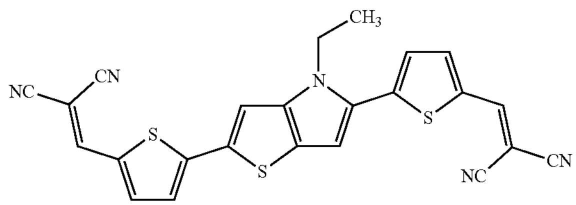 [SMILES: CCn1c(-c2ccc(C=C(C#N)C#N)s2)cc2sc(-c3ccc(C=C(C#N)C#N)s3)cc21] | 330 | 543[b] | 2.28[b] |
| F5 | 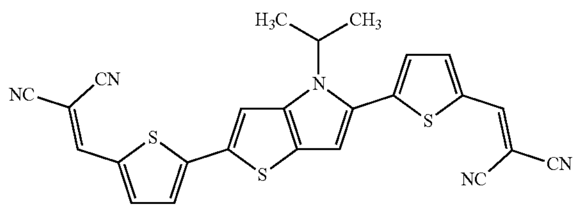 | 343 | 540[c] | 2.30[c] |
| F6 | 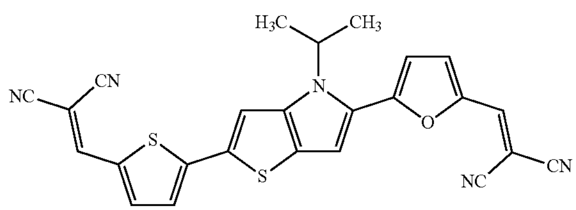 [SMILES: CC(C)n1c(-c2ccc(C=C(C#N)C#N)o2)cc2sc(-c3ccc(C=C(C#N)C#N)s3)cc21] | nd | 558[c] | 2.22[c] |
| F7 | 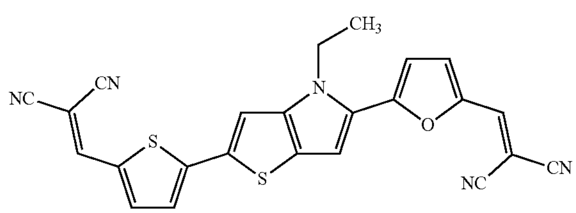 | nd | | |
| F8 | 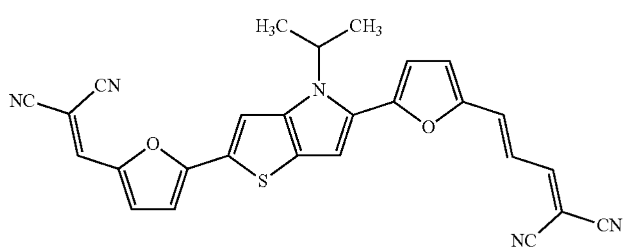 [SMILES: CC(C)n1c(-c2ccc(/C=C/C=C(C#N)C#N)o2)cc2sc(-c3ccc(C=C(C#N)C#N)o3)cc21] | nd | | |
| F9 | 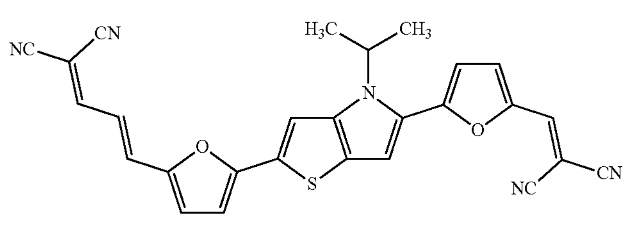 [SMILES: CC(C)n1c(-c2ccc(C=C(C#N)C#N)o2)cc2sc(-c3ccc(/C=C/C=C(C#N)C#N)o3)cc21] | nd | | |

TABLE 1-continued

| No. | Structure | m.p./° C.[a] approx. | λmax (SO)/nm[b] | λmax (SO)/eV[b] |
|---|---|---|---|---|
| F10 | [structure: bis(dicyanovinyl-furan-vinyl) substituted N-isopropyl thienopyrrole] | 325 | 597[b] | 2.08[b] |
| F11 | [structure: bis(dicyanovinyl-thiazole) substituted N-isopropyl thienopyrrole] | 314 | 534[b] | 2.32[b] |
| F12 | [structure: bis(dicyanovinyl-furan-vinyl) substituted N-phenyl thienopyrrole] | 291 | 555[b] | 2.23[b] |

[a] onset DSC (dynamic differential calorimetry)
[b] in dichloromethane

The optical properties were determined experimentally. The absorption maxima λmax were determined with a dilute solution in a cuvette in dichloromethane using a photometer. The measured absorption maxima of all the compounds described are within a range from 534 to 597 nm.

Table 2 shows various parameters of compounds F3, F6, and F12 of the invention and of comparison compound F1. The parameters open-circuit voltage Uoc, short-circuit current Jsc, and fill factor FF relate in each case to the same structure of a solar cell.

To investigate the compounds, i.e. the use thereof as absorber materials in organic optoelectronic components, the current-voltage curve was measured in a BHJ cell having the structure: glass with ITO/C60 (15 nm)/absorber material: C60 (30 nm, 3:2, 50° C.)/BPAPF (10 nm)/BPAPF:NDP9 (30 nm, 10% by weight NDP9)/NDP9 (1 nm)/Al (100 nm) under AM1.5 illumination (AM=air mass; AM=1.5 spectrum the global radiation power is 1000 W/m$^2$; AM=1.5 as standard value for the measurement of solar modules), the photoactive layer being a bulk heterojunction (BHJ). A transparent cover contact made of ITO (indium tin oxide) is applied to a glass substrate. ITO serves here as the electrode, and the neighboring fullerene C60 as the electron-transport layer (ETL), adjoining this is the photoactive C60 layer as electron acceptor material and the respective compound, followed by BPAPF (9,9-bis[4-(N,N-bis-biphenyl-4-yl-amino)phenyl]-9H-fluorene) as a hole-transport layer (HTL) and BPAPF doped with NDP9 (Novaled AG), followed by an electrode made of aluminum.

The advantageous technical effect of compounds of the invention that have a central thienopyrrole moiety or a central furopyrrole moiety, in particular a central thienopyrrole moiety, interacting with a furan group or a thiophene group, in particular a furan group, on the pyrrole of the central thienopyrrole moiety or of the central furopyrrole moiety, and which have a sterically demanding group on the N of the pyrrole of the central thienopyrrole moiety or of the central furopyrrole moiety, is by way of example illustrated below in Table 2 with reference to compounds F3, F6, and F12 in comparison with a comparison compound F1. The experimental data for compounds F3 and F12 are shown in FIGS. 3 and 4.

TABLE 2

| Substance | Slope | Uoc [V] | Jsc/EQE [mA/cm²] | FF [%] |
|---|---|---|---|---|
| F1 (structure) | 2.75 | 0.81 | 7.5 | 47.0 |
| F3 (structure) | 9.72 | 0.91 | 15.1 | 68.9 |
| F6 (structure) | 5.76 | | | |
| F12 (structure) | 5.9 | 0.97 | 10.3 | 46.6 |

The particularly advantageous properties of the compounds of the invention are demonstrated, in an identical solar cell structure, also in the parameters open-circuit voltage Uoc, short-circuit current Jsc, and fill factor FF. The compounds of the invention have not only improved absorption properties, but also suitable charge-transport properties. As a function of the charge-transport properties and the absorption properties, it is possible to achieve high photocurrents with good fill factors. This allows particularly good combinations of photoactive layers to be produced, in particular for tandem, triple, quadruple or multiple solar cells.

In a particularly preferred embodiment, the compounds of the invention have a central thienopyrrole moiety having a furan ring on the pyrrole of the central thienopyrrole moiety together with a sterically demanding group on the N of the pyrrole ring of the central thienopyrrole moiety; compounds F3 and F6 are shown by way of example in Table 2.

FIG. 1 shows an exemplary embodiment of a synthesis scheme for the synthesis of compounds of the invention.

The preparation of the compound of the invention is known to those skilled in the art from the prior art. Reference in this context is made in particular to international patent applications WO2017114937A1 and WO2017114938A1. The compounds of the invention are thus accessible in a simple manner and in good yields. A general synthesis for preparing a compound of the invention is shown below by way of example.

The compound of the invention having the general formula I

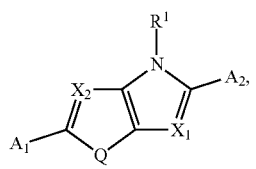

is characterized in that

Q is O or S, preferably Q is S;

R1 is selected from the group consisting of alkoxy, alkyl, fluorinated alkyl, partially fluorinated alkyl, and aryl;

X1 and X2 are independently of one another N or C—R4; where

R4 is selected from the group consisting of H, halogen, alkoxy, branched or linear, cyclic or open-chain alkyl, alkenyl, and aryl, wherein H may in each case be substituted;

A1 is a group having the formula Ia

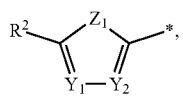

where * denotes the point of attachment to the compound of the general formula I; Z1 is selected from the group consisting of O, S, Se, and N—R5, where R5 is selected from the group consisting of H, alkoxy, alkyl, fluorinated alkyl, partially fluorinated alkyl, and aryl; Y1 is N or C—R6, where R6 is selected from the group consisting of H, halogen, alkoxy, branched or linear, cyclic or open-chain alkyl, alkenyl, and aryl, wherein H may in each case be substituted; Y2 is N or C—R7, where R7 is selected from the group consisting of H, halogen, alkoxy, branched or linear, cyclic or open-chain alkyl, alkenyl, and aryl, wherein H may in each case be substituted; and where R6 and R7 may be homocyclically or heterocyclically linked to one another in the form of a ring structure; R2 is selected from the group consisting of H, halogen, alkoxy, alkyl, fluorinated alkyl, partially fluorinated alkyl, branched or linear, cyclic or open-chain alkyl, amino, aryl, heteroaryl, alkenyl, and an electron-withdrawing alkyl group having at least one C=C double bond, wherein H may be substituted by CN or F; A2 is a group having the formula Ib

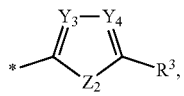

where * denotes the point of attachment to the compound of the general formula I; Z2 is selected from the group consisting of O, S, Se, and N—R8, where R8 is selected from the group consisting of H, alkoxy, alkyl, fluorinated alkyl, partially fluorinated alkyl, and aryl; Y3 is N or C—R9, where R9 is selected from the group consisting of H, halogen, alkoxy, branched or linear, cyclic or open-chain alkyl, alkenyl, and aryl, wherein H may in each case be substituted; Y4 is N or C—R10, where R10 is selected from the group consisting of H, halogen, alkoxy, branched or linear, cyclic or open-chain alkyl, alkenyl, and aryl, wherein H may in each case be substituted; and where R9 and R10 may be homocyclically or heterocyclically linked to one another in the form of a ring structure; R3 is selected from the group consisting of H, halogen, alkoxy, alkyl, fluorinated alkyl, partially fluorinated alkyl, branched or linear, cyclic or open-chain alkyl, amino, aryl, heteroaryl, alkenyl, and an electron-withdrawing alkyl group having at least one C=C double bond, wherein H may be substituted by CN or F.

Improved absorption properties, particularly when there is a steep absorption in the bathochromic region, in conjunction with very good charge-transport properties makes it possible to generate high photocurrents. This allows the production in particular of tandem, triple, quadruple or multiple cells.

In one configuration of the invention, R1 is selected from the group consisting of ethyl, propyl, butyl, branched alkyl, and aryl, preferably from isopropyl, isobutyl, sec-butyl, tert-butyl, isopentyl and phenyl; and where Z1 and Z2 are each independently of one another O or S, preferably Z2 is O. This realizes the advantageous effects of the present invention in a particular way.

In another configuration of the invention, the compound is a compound of the general formula II,

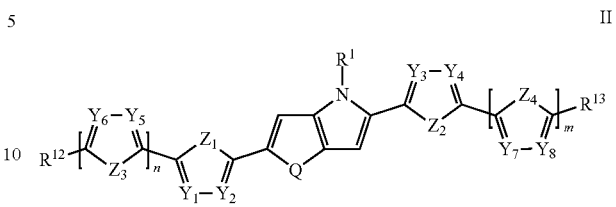

where n is 0, 1 or 2 and m is 0, 1 or 2;
Q is O or S, preferably Q is S; Z3 and Z4 are each independently of one another selected from the group consisting of O, S, Se, and N—R11, where R11 is selected from the group consisting of H, alkoxy, alkyl, fluorinated alkyl, partially fluorinated alkyl, and aryl; R12 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F;
R13 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F; Y5 is N or C—R14, where R14 is selected from the group consisting of H, halogen, alkoxy, alkyl, and alkenyl, wherein H may in each case be substituted, where Y5 is preferably N, CH or CF; Y6 is N or C—R15, where R15 is selected from the group consisting of H, halogen, alkoxy, alkyl, and alkenyl, wherein H may in each case be substituted, where Y6 is preferably N, CH or CF; Y7 is N or C—R16, where R16 is selected from the group consisting of H, halogen, alkoxy, alkyl, and alkenyl, wherein H may in each case be substituted, where Y7 is preferably N, CH or CF; Y8 is N or C—R17, where R17 is selected from the group consisting of H, halogen, alkoxy, alkyl, and alkenyl, wherein H may in each case be substituted, where Y8 is preferably N, CH or CF; and where respectively R14 and R15, and/or R16 and R17, may together form a homocyclic five-membered ring or six-membered ring, or a heterocyclic five-membered ring or six-membered ring containing at least one heteroatom selected from the group consisting of S, O, and N.

In another configuration of the invention, R14 and R15 together and/or R16 and R17 together form a homocyclic five-membered ring or six-membered ring, or a heterocyclic five-membered ring or six-membered ring containing at least one heteroatom selected from the group consisting of S, O, and N.

In another configuration of the invention, Z3 and Z4 are independently of one another O or S.

In another configuration of the invention, A1 is a group having the formula IIa

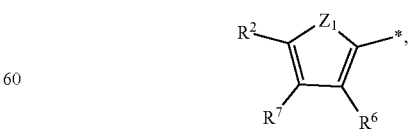

where R6 is selected from the group consisting of H, halogen, alkoxy, branched or linear, cyclic or open-chain alkyl, alkenyl, and aryl, wherein H may in each case be substituted;

R7 is selected from the group consisting of H, halogen, alkoxy, branched or linear, cyclic or open-chain alkyl, alkenyl, and aryl, wherein H may in each case be substituted; and where R6 and R7 may together form a homocyclic five-membered ring or six-membered ring, or a heterocyclic five-membered ring or six-membered ring containing at least one heteroatom selected from the group consisting of S, O and N;

and A2 is a group having the formula IIb

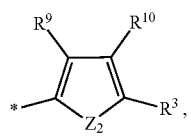

where R9 is selected from the group consisting of H, halogen, alkoxy, branched or linear, cyclic or open-chain alkyl, alkenyl, and aryl, wherein H may in each case be substituted;

R10 is selected from the group consisting of H, halogen, alkoxy, branched or linear, cyclic or open-chain alkyl, alkenyl, and aryl, wherein H may in each case be substituted; and where R9 and R10 may together form a homocyclic five-membered ring or six-membered ring, or a heterocyclic five-membered ring or six-membered ring containing at least one heteroatom selected from the group consisting of S, O and N.

In another configuration of the invention, the compound is a compound of the general formula III, IV, and/or V,

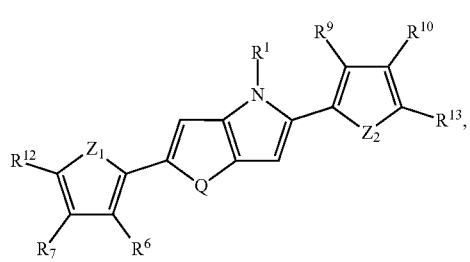

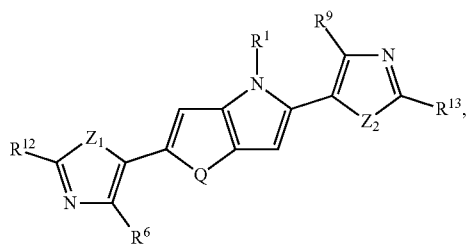

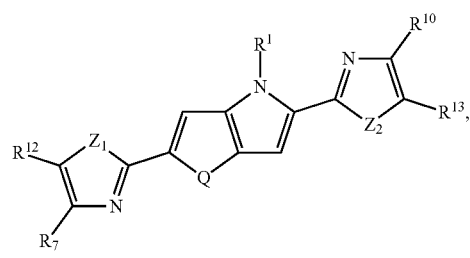

where Q is O or S, preferably Q is S; Z1 and Z2 are each independently of one another O or S, preferably Z2 is O; R6 is selected from the group consisting of H, halogen, alkoxy, alkyl, and alkenyl, wherein H may in each case be substituted;

R7 is selected from the group consisting of H, halogen, alkoxy, alkyl, and alkenyl, wherein H may in each case be substituted; and where R6 and R7 may together form a homocyclic five-membered ring or six-membered ring, or a heterocyclic five-membered ring or six-membered ring containing at least one heteroatom selected from the group consisting of S, O and N; R9 is selected from the group consisting of H, halogen, alkoxy, alkyl, and alkenyl, wherein H may in each case be substituted; R10 is selected from the group consisting of H, halogen, alkoxy, alkyl, and alkenyl, wherein H may in each case be substituted; and where R9 and R10 may together form a homocyclic five-membered ring or six-membered ring, or a heterocyclic five-membered ring or six-membered ring containing at least one heteroatom selected from the group consisting of S, O and N; R12 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F; and R13 is selected from the group consisting of H, alkoxy, alkyl, fluorinated alkyl, partially fluorinated alkyl, alkenyl, and an electron-withdrawing alkyl group having at least one C=C double bond, wherein H may be substituted by CN or F.

In another configuration of the invention, R2 and R3, or R12 and R13, are each independently of one another

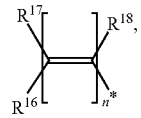

where n is 1, 2 or 3, where * denotes the point of attachment of the group R2, R3, R12 and/or R13; R16, R17, and R18 are each independently of one another selected from the group consisting of H, halogen, CN, COO-alkyl, alkyl, and alkenyl, with the proviso that R16 and R17 are not both H, R16 and R17 preferably being CN.

In another configuration of the invention, R2 and R3, or R12 and R13, are each independently of one another selected from the group consisting of:

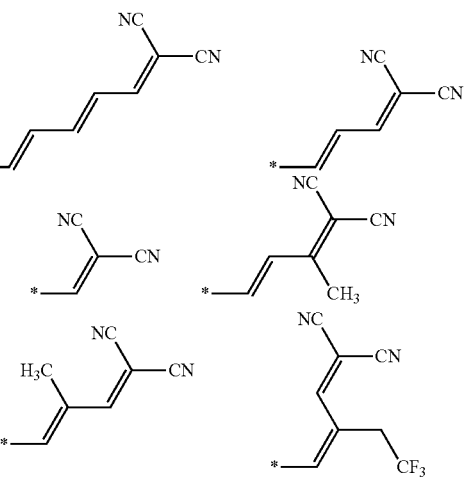

-continued

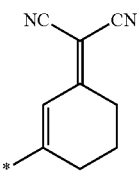 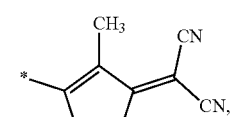

where * denotes the point of attachment of the group R2, R3, R12 and/or R13, in which CN may be replaced by F and where R2 and R3, or R12 and R13, are preferably identical.

In another configuration of the invention, R6 and R7 are H, R9 and R10 are H, and Z2 is O, wherein Z1 and Z2 are preferably O.

In another configuration of the invention, the compound is selected from the group consisting of:

F3

[structure]

F4

[structure]

F5

[structure]

F6

[structure]

F7

[structure]

-continued

F8

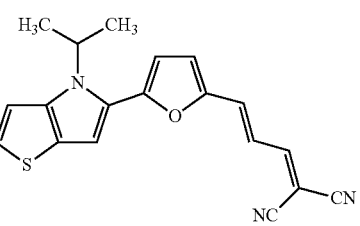

F9

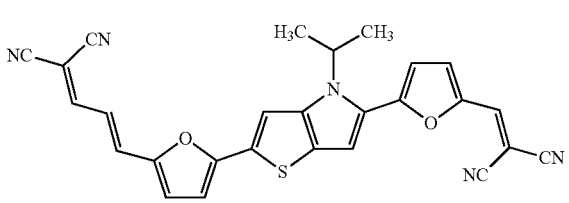

F10

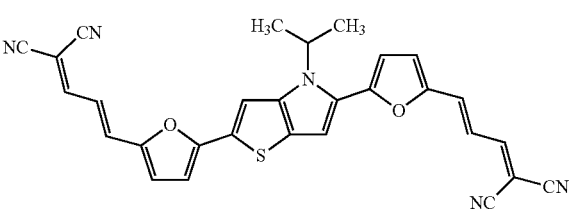

F11

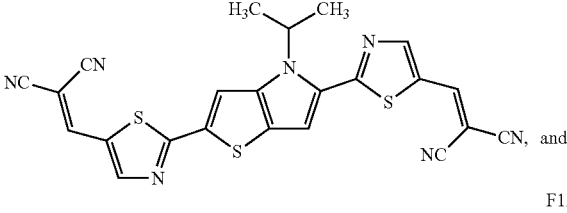

F12

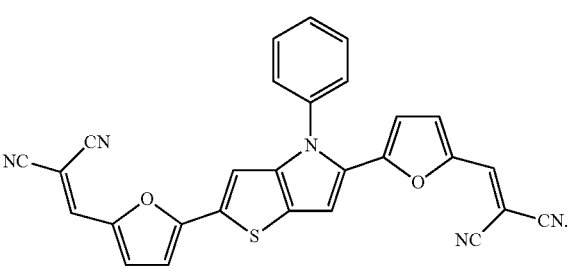

, and

[structure]

In another configuration of the invention, group A1 is the same as group A2.

Figure 2:
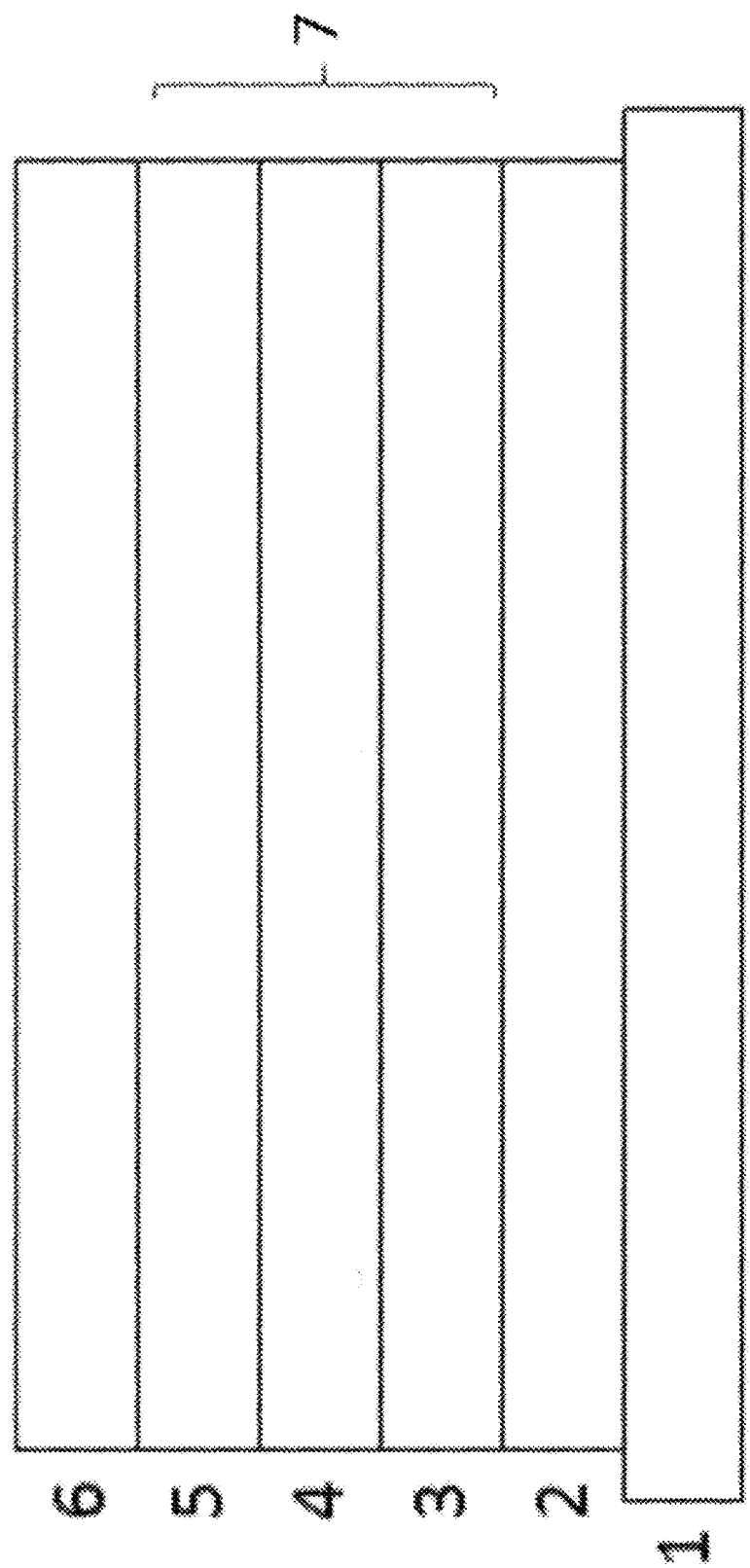
FIG. 2 shows a schematic representation of an exemplary embodiment of an optoelectronic component in cross section.

FIG. 2 shows a schematic representation of an exemplary embodiment of an optoelectronic component in cross section.

The optoelectronic component comprises a first electrode 2, a second electrode 6, and a layer system 7, the layer system 7 being arranged between the first electrode 2 and the second electrode 6. At least one layer of the layer system 7 comprises at least one compound of the invention.

In one configuration of the invention, the optoelectronic component is an organic optoelectronic component, preferably an organic solar cell, an OFET, an OLED or an organic photodetector.

In this exemplary embodiment, the optoelectronic component is an organic solar cell. The organic solar cell has a substrate 1, made e.g. of glass, on which there is an electrode 2, that e.g. includes ITO. Arranged thereon is a layer system 7 having an electron-transporting layer 3 (ETL) and a photoactive layer 4 comprising at least one compound of the invention, a p-conducting donor material, and an n-conducting acceptor material, e.g. C60 fullerene, either as a planar heterojunction or as a bulk heterojunction. Arranged above this is a p-doped hole-transport layer 5 (HTL) and an electrode 6 made of aluminum.

In another configuration of the invention, the layer system 7 has at least one photoactive layer 4, preferably an absorber layer, the at least one photoactive layer 4 comprising the at least one compound of the invention.

In another configuration of the invention, the layer system 7 has at least two photoactive layers, preferably at least three photoactive layers, or preferably at least four photoactive layers.

In another configuration of the invention, the photoactive layer 4 is formed as a mixed layer of the at least one compound of the invention and at least one further compound, or as a mixed layer of the at least one compound of the invention and at least two further compounds, the compounds being absorber materials.

In another configuration of the invention, the optoelectronic component is formed as a tandem cell, triple cell or multiple cell.

FIGS. 3 and 4 below illustrate specific exemplary embodiments of the compounds of the invention and the optical properties thereof.

Figure 3A:
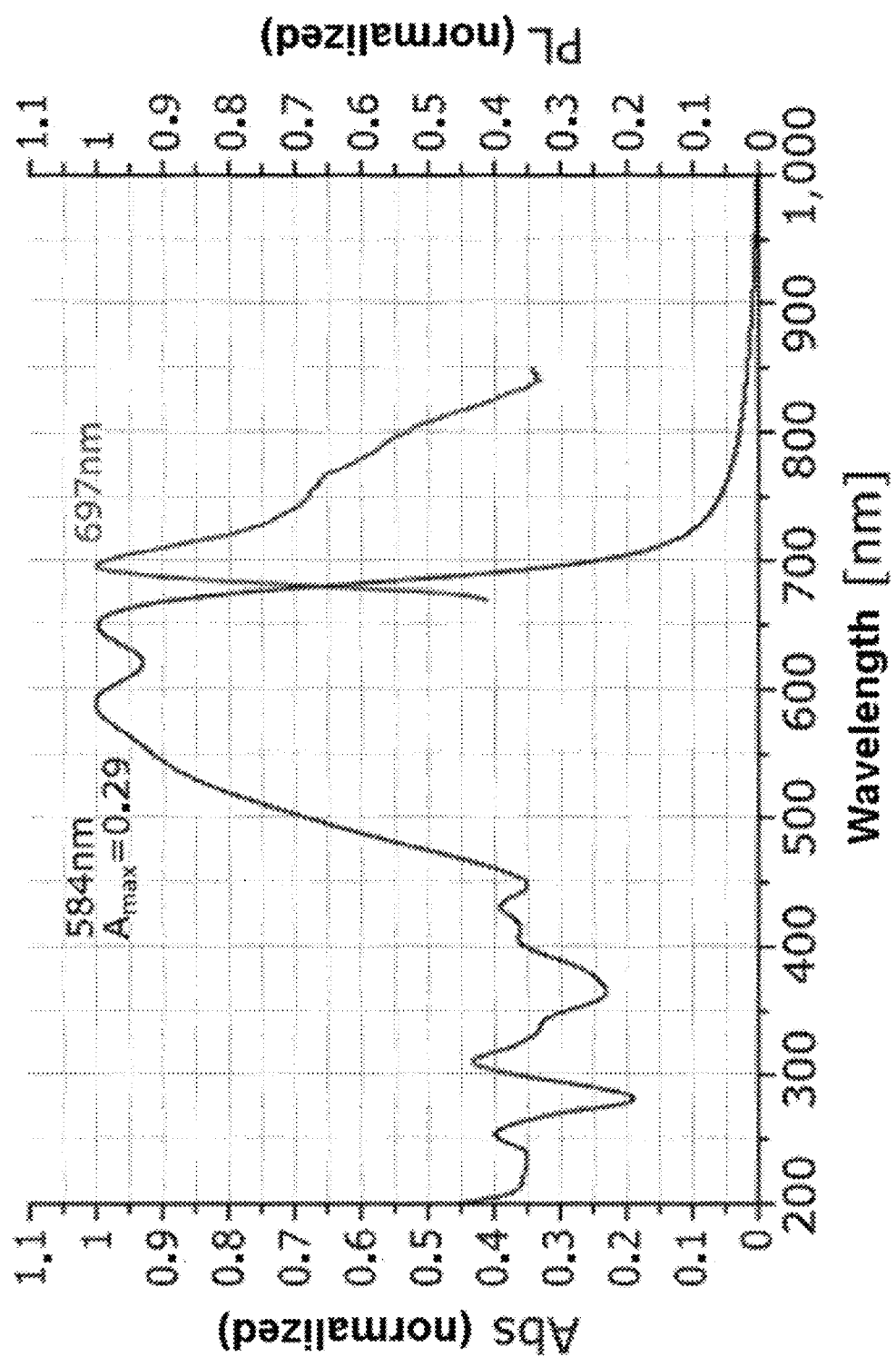
FIGS. 3A, 3B, 3C, and 3D show a graphical representation of the absorption spectrum of compound F3, and of the current-voltage curve, of the spectral external quantum yield, and of the fill factor of a BHJ cell comprising compound F3, measured on an organic optoelectronic component in the form of an organic solar cell.
Figure 3C:
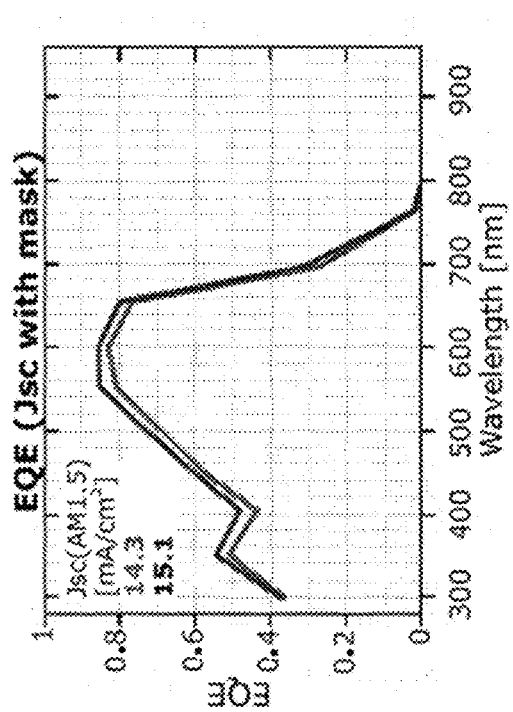
Figure 3D:
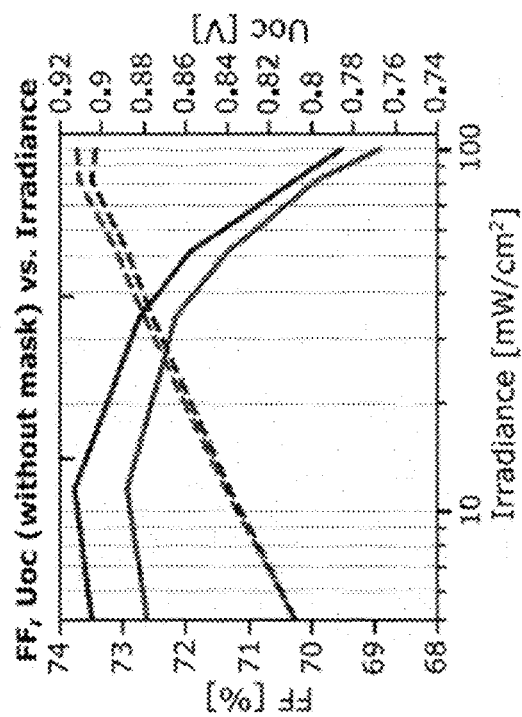
Figure 3B:
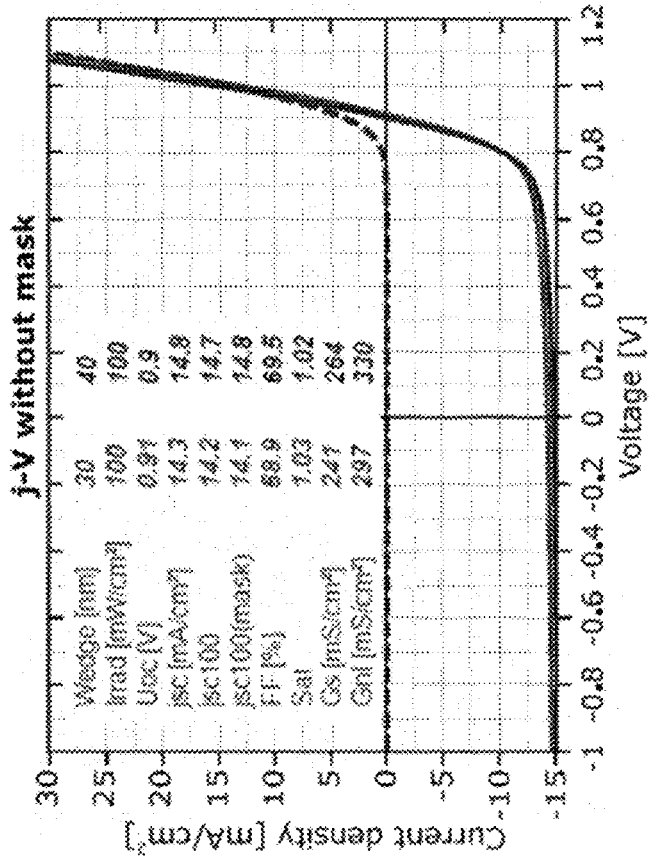

FIG. 3A shows a graphical representation of the absorption spectrum of compound F3, FIG. 3B shows the current-voltage curve, FIG. 3 shows the spectral external quantum yield, and FIG. 3D shows the fill factor of a BHJ cell comprising compound F3, measured on an organic optoelectronic component in the form of an organic solar cell.

The absorption spectra (optical density over wavelength in nm) of compounds F3, F12 and the comparison compound F1 were measured as vacuum-deposited layers having a thickness of 30 nm, in each case on quartz glass. The current-voltage curve comprises indicators that characterize the organic solar cell. The most important indicators here are the fill factor FF, the open-circuit voltage Uoc, and the short-circuit current Jsc.

The absorption spectrum of compound F3 is shown in FIG. 3A. Compound F3 shows a particularly steep absorption curve in the bathochromic region, that is to say on the flank in the higher wavelength region of the absorption spectrum, with a slope of 9.72. The slope of the curve in the absorption spectrum is determined via the gradient of the tangent at the inflection point that occurs between the start of the absorption and the first edge of the absorption. The bathochromic region is understood as meaning in particular a region shifted into the red wavelength range of visible light, that is to say into the longer-wavelength, lower-energy range of the electromagnetic spectrum. This steep curve in the bathochromic region of the absorption spectrum is particularly advantageous in the formation of tandem, triple or multiple cells.

In this exemplary embodiment, the BHJ cell on the ITO layer has a layer of C60 with a layer thickness of 15 nm. Onto this layer was applied compound F3 together with C60 in a thickness of 30 nm. Said layer is followed by a layer of BPAPF (9,9-bis[4-(N,N-bis-biphenyl-4-yl-amino)phenyl]-9H-fluorene) in a layer thickness of 10 nm, on top of which there is a further layer comprising BPAPF and NDP9 in a layer thickness of 30 nm. The proportion of BPAPF in this layer is 10 percent by weight based on the entire layer. Adjoining this layer is a further layer comprising NDP9 in a thickness of 1 nm, this being followed by an aluminum layer in a thickness of 100 nm. The current-voltage curve of a BHJ cell having the structure: ITO/C60 (15 nm)/F3:C60 (30 nm, 3:2, 50° C.)/BPAPF (10 nm)/BPAPF:NDP9 (30 nm, 10% by weight NDP9)/NDP9 (1 nm)/A1 (100 nm) was determined, the photoactive layer being a bulk heterojunction (BHJ). In the optoelectronic component comprising compound F3, the fill factor FF is 68.9%, the open-circuit voltage Uoc is 0.91 V, and the short-circuit current Jsc is 15.1 mA/cm2 (FIG. 3B). The cell efficiency of an optoelectronic component of this type, in particular a solar cell, comprising compound F3 is 9.4%.

Compound F3 also shows good vaporizability under reduced pressure.

Figure 4A:
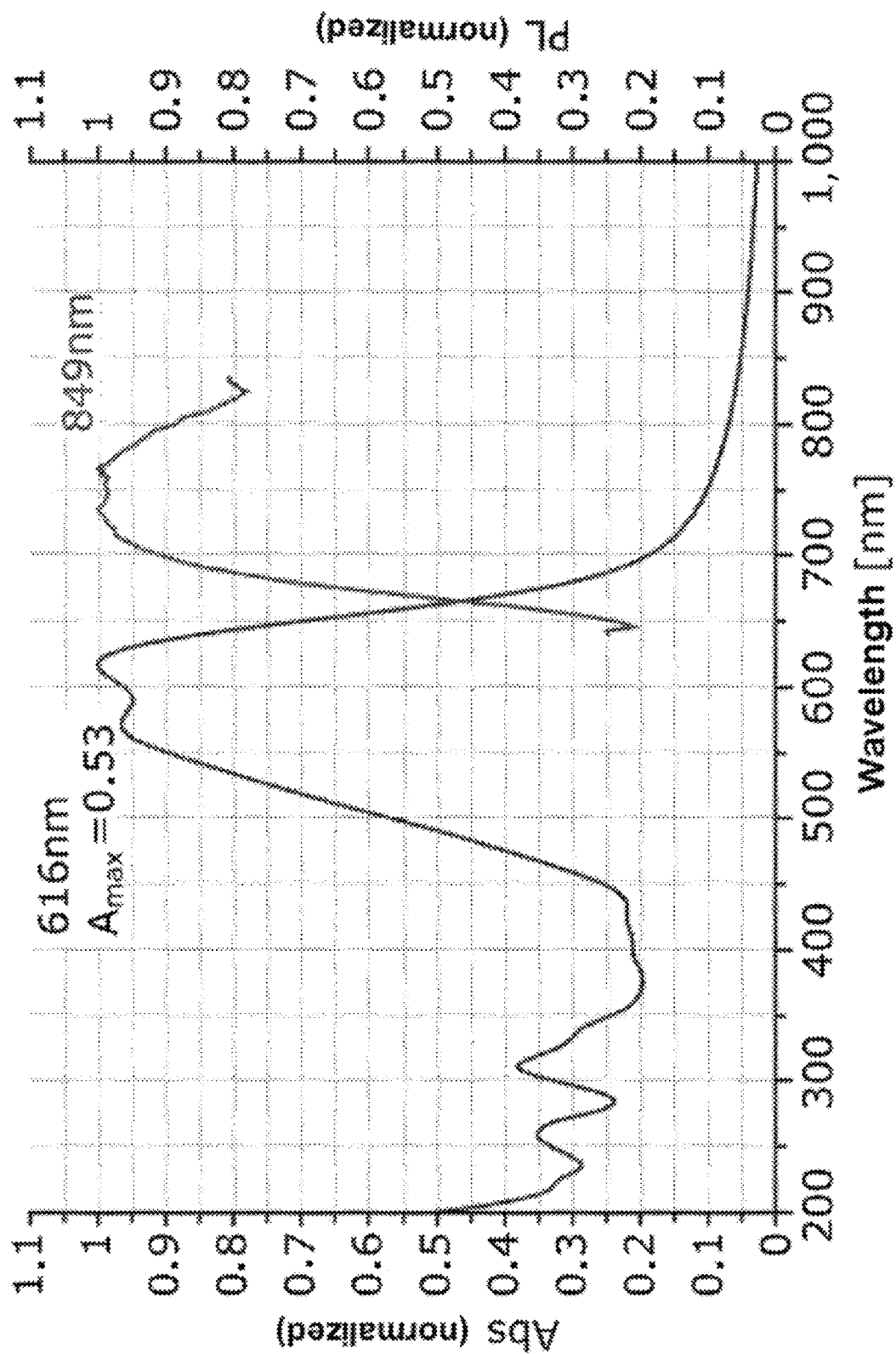
FIGS. 4A, 4B, 4C, and 4D show a graphical representation of the absorption spectrum of compound F12, and of the current-voltage curve of the spectral external quantum yield, and of the fill factor of a BHJ cell comprising compound F12, measured on an organic optoelectronic component in the form of an organic solar cell.
Figure 4C:
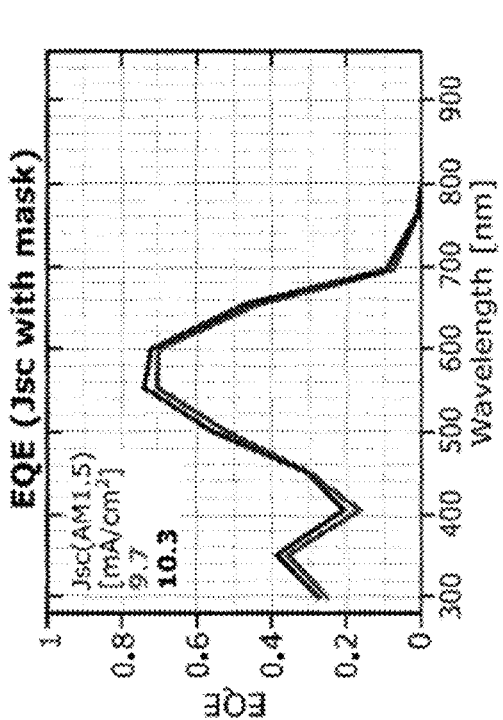
Figure 4D:
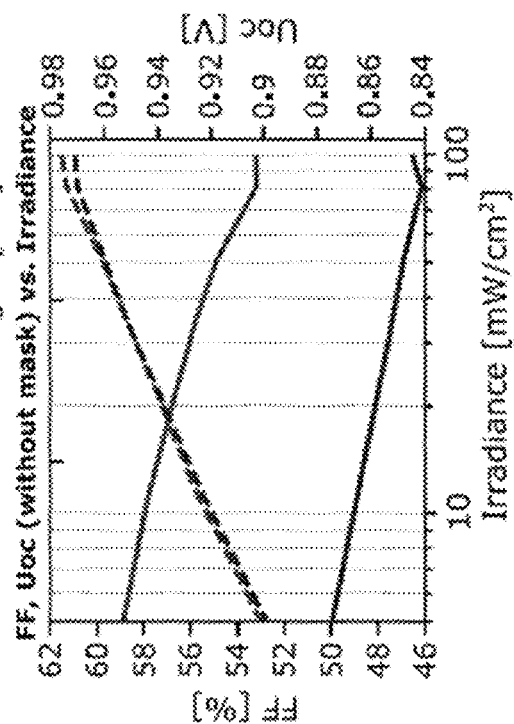
Figure 4B:
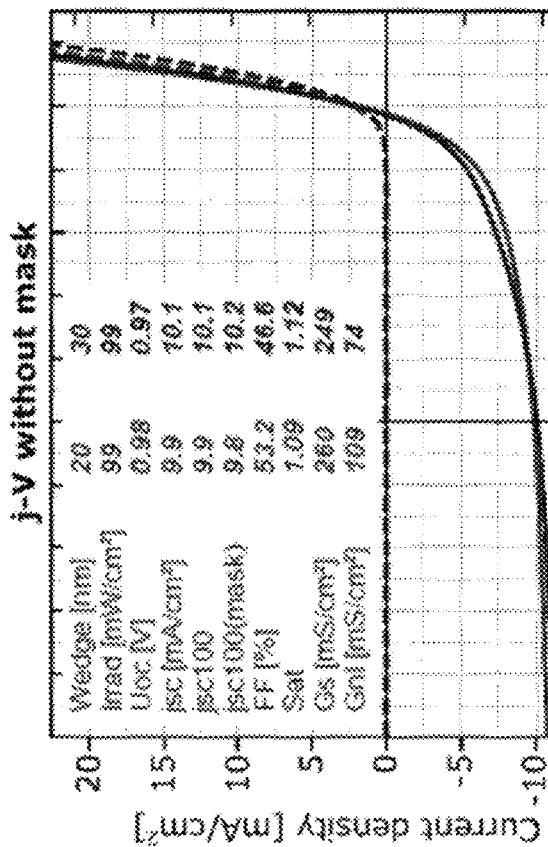

FIG. 4 shows a graphical representation of the absorption spectrum of compound F12, FIG. 4B shows the current-voltage curve, FIG. 4C shows the spectral external quantum yield, and FIG. 4D shows the fill factor of a BHJ cell comprising compound F12, measured on an organic optoelectronic component in the form of an organic solar cell.

The absorption spectrum of compound F12 is shown in FIG. 4A. Like compound F3 previously, compound F12 shows a particularly steep absorption curve with a slope of 5.9.

The current-voltage curve of a BHJ cell having the structure: ITO/C60 (15 nm)/F12:C60 (30 nm, 3:2, 50° C.)/BPAPF (10 nm)/BPAPF:NDP9 (30 nm, 10% by weight NDP9)/NDP9 (1 nm)/A1 (100 nm) was determined, the photoactive layer being a bulk heterojunction (BHJ). In the optoelectronic component comprising compound F12, the fill factor FF is 46.6%, the open-circuit voltage Uoc is 0.97 V, and the short-circuit current Jsc is 10.3 mA/cm2 (FIG. 4B). The cell efficiency of an optoelectronic component of this type, in particular a solar cell, comprising compound F12 is 4.7%.

Compound F12 also shows good vaporizability under reduced pressure.

The experimental data of compounds F3 and F12 with the absorption properties and the current-voltage curves measured in organic solar cells demonstrate that compounds F3 and F12 are very well suited for use in organic solar cells and other organic optoelectronic components.

Figure 5A:
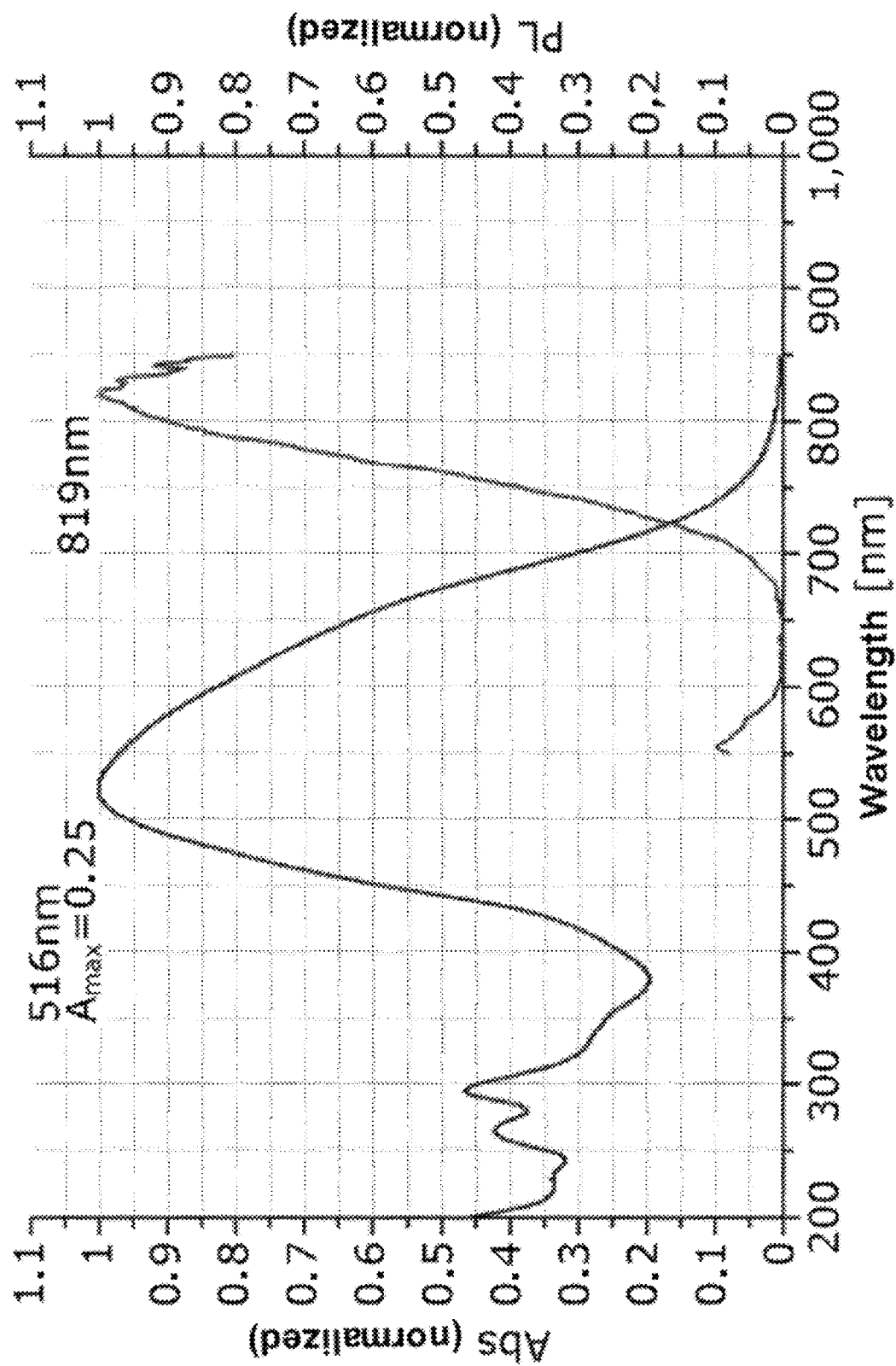

FIG. 5A shows a graphical representation of the absorption spectrum of comparison compound F1, FIG. 5B shows the current-voltage curve, FIG. 5C shows the spectral external quantum yield, and FIG. 5D shows the fill factor of a BHJ cell comprising comparison compound F1, measured on an organic optoelectronic component in the form of an organic solar cell.

Compound F1 shows a flattened absorption curve, with a slope of 2.75.

The current-voltage curve of a BHJ cell having the structure: ITO/C60 (15 nm)/F1:C60 (30 nm, 3:2, 50° C.)/ BPAPF (10 nm)/BPAPF:NDP9 (30 nm, 10% by weight NDP9)/NDP9 (1 nm)/A1 (100 nm) was determined, the photoactive layer being a bulk heterojunction (BHJ). In the optoelectronic component comprising compound F1, the fill factor FF is 47.0%, the open-circuit voltage Uoc is 0.81 V, and the short-circuit current Jsc is 7.5 mA/cm2.

The experimental data of the comparison compound F1 and compounds F3 and F12 show that compounds F3 and F12 have better absorption properties compared to the comparison compound F1.

Figure 6:
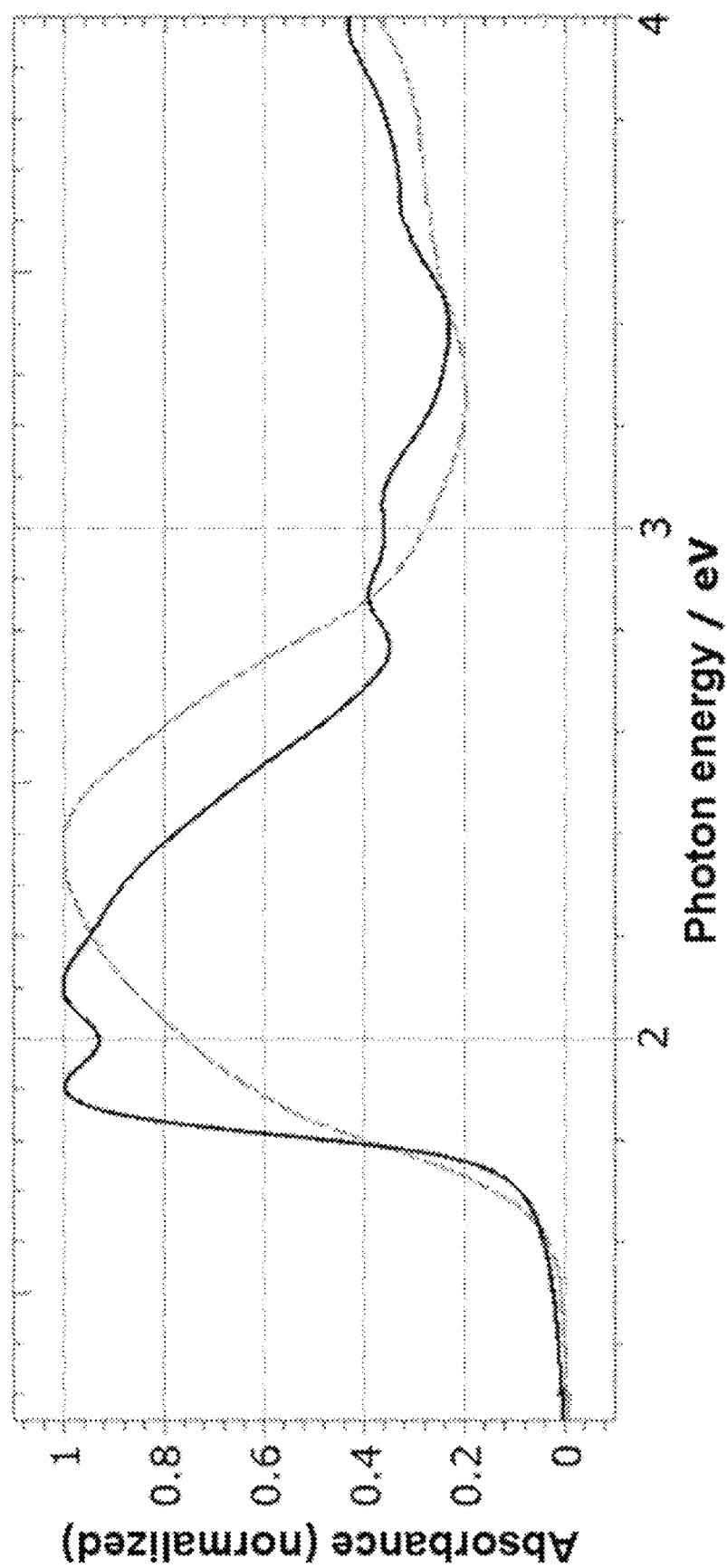
FIG. 6 shows a graphical representation of a comparison of the absorption spectrum of compound F3 with a comparison compound F1.

FIG. 6 shows a graphical representation of a comparison of the absorption spectrum of compound F3 with a comparison compound F1.

The absorption of compound F3 (shown with a solid line) and of comparison compound F1 (shown with a dashed line) is plotted against the photon energy. It can be clearly seen that the absorption of compound F3, having a slope of 9.72, is significantly steeper than that of comparison compound F1, having a slope of 2.75.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. An optoelectonic component comprising at least one compound of the general formula III, IV, or V,

III

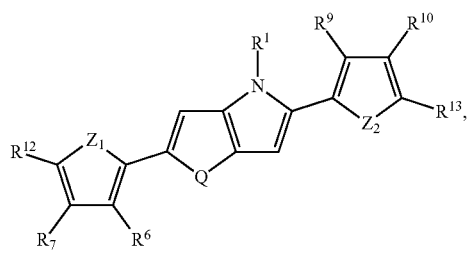

IV

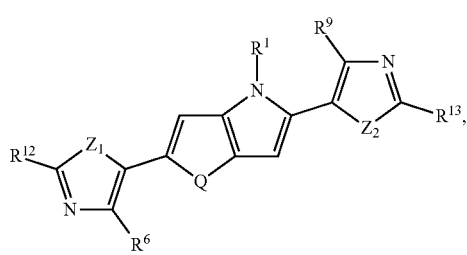

V

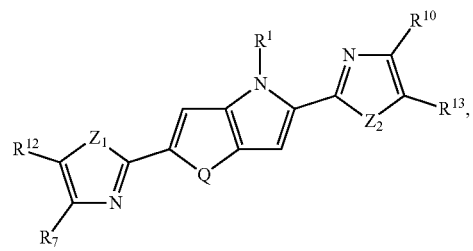

wherein:

Q is S;

R1 is selected from the group consisting of alkyl, fluorinated alkyl, and aryl, wherein R1 is sterically larger than a methyl group;

R6 is selected from the group consisting of H, halogen, alkoxy, alkyl, and alkenyl, wherein H may in each case be substituted;

R7 is selected from the group consisting of H, halogen, alkoxy, alkyl, and alkenyl, wherein H may in each case be substituted; and where R6 and R7 may together form a homocyclic five-membered ring or six-membered ring, or a heterocyclic five-membered ring or six-membered ring containing at least one heteroatom selected from the group consisting of S, O, and N;

R9 is selected from the group consisting of H, halogen, alkoxy, alkyl, and alkenyl, wherein H may in each case be substituted;

R10 is selected from the group consisting of H, halogen, alkoxy, alkyl, and alkenyl, wherein H may in each case be substituted; and where R9 and R10 may together form a homocyclic five-membered ring or six-membered ring, or a heterocyclic five-membered ring or six-membered ring containing at least one heteroatom selected from the group consisting of S, O, and N;

R12 is selected from the group consisting of:

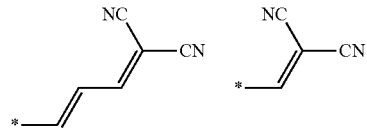 [SMILES: */C=C/C=C(C#N)C#N ; *C=C(C#N)C#N]

R13 is selected from the group consisting of:

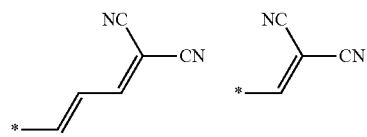 [SMILES: */C=C/C=C(C#N)C#N ; *C=C(C#N)C#N]

Z1 is O or S; and

Z2 is O or S.

2. The optoelectronic component as claimed in claim 1, wherein:

R6 and R7 are H, R9 and R10 are H, and Z2 is O.

3. The optoelectronic component as claimed in claim 1, wherein the compound is selected from the group consisting of:

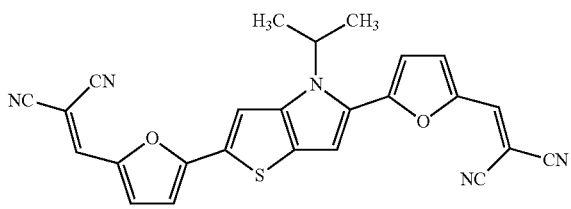
F3

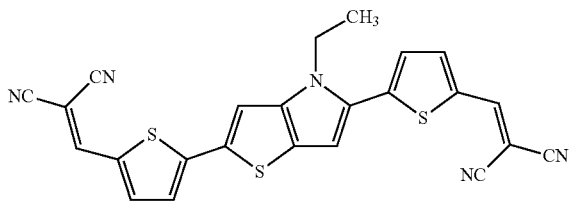
F4

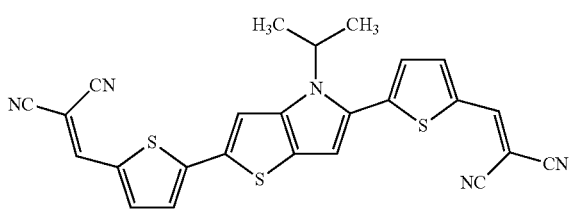
F5

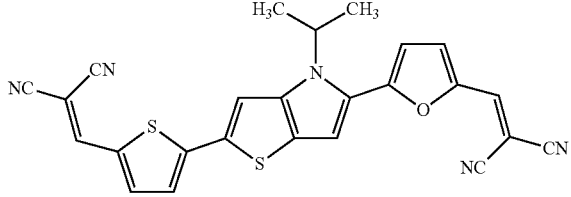
F6

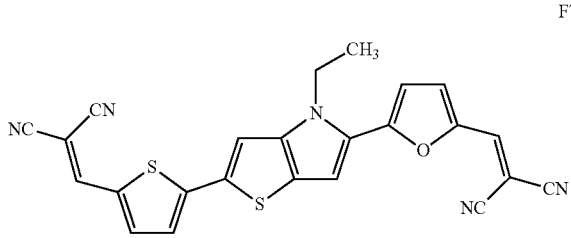
F7

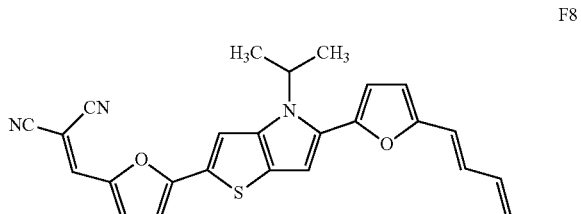
F8

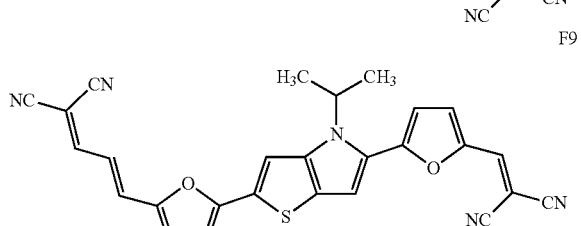
F9

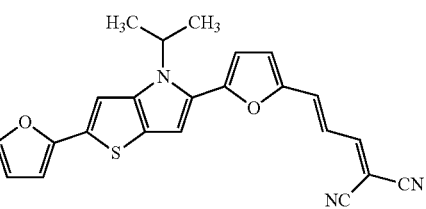
F10

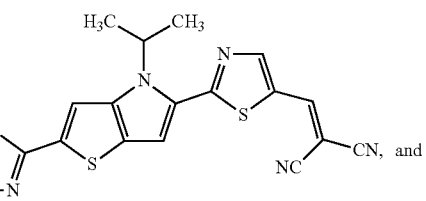
F11

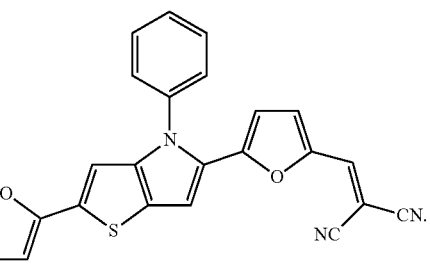
F12

4. The optoelectronic component as claimed in claim 1, wherein the optoelectronic component comprises a first electrode (2), a second electrode (6), and a layer system (7), the layer system being arranged between the first electrode (2) and the second electrode (6), wherein at least one layer of the layer system (7) comprises the at least one compound.

5. The optoelectronic component as claimed in claim 4, wherein the optoelectronic component is an organic optoelectronic component selected from an organic solar cell, an OFET, an OLED or an organic photodetector.

6. The optoelectronic component as claimed in claim 1, wherein the optoelectronic component comprises a first electrode, a second electrode, and a layer system, the layer system being arranged between the first electrode and the second electrode, wherein at least one layer of the layer system is a photoactive layer, the photoactive layer comprising the at least one compound.

7. The optoelectronic component as claimed in claim 6, wherein the photoactive layer comprises the at least one compound and at least two absorber materials.

8. The optoelectronic component as claimed in claim 1, wherein R1 is selected from the group consisting of isopropyl, isobutyl, sec-butyl, isopentyl, tert-butyl and phenyl.

9. The optoelectronic component as claimed in claim 1, wherein Z2 is O.

10. The optoelectronic component as claimed in claim 1, wherein Z1 is S.

11. The optoelectronic component as claimed in claim 10, wherein Z2 is S.

12. The optoelectronic component as claimed in claim 1, wherein the optoelectronic component is an organic solar cell.

\* \* \* \* \*